US 12,178,870 B2
(12) United States Patent
Wong et al.

(10) Patent No.: US 12,178,870 B2
(45) Date of Patent: Dec. 31, 2024

(54) CHIMERIC INFLUENZA VACCINES

(71) Applicant: ACADEMIA SINICA, Taipei (TW)

(72) Inventors: Chi-Huey Wong, Rancho Santa Fe, CA (US); Hsin-Yu Liao, New Taipei (TW); Shih-Chi Wang, New Taipei (TW); Yi-An Ko, Taipei (TW); Kuo-I Lin, Taipei (TW); Che Ma, New Taipei (TW); Ting-Jen Cheng, New Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 18/662,436

(22) Filed: May 13, 2024

(65) Prior Publication Data

US 2024/0316179 A1    Sep. 26, 2024

Related U.S. Application Data

(63) Continuation of application No. 18/501,578, filed on Nov. 3, 2023, now Pat. No. 11,992,525, which is a continuation of application No. 17/998,208, filed as application No. PCT/US2021/031406 on May 7, 2021, now Pat. No. 11,918,641.

(60) Provisional application No. 63/022,328, filed on May 8, 2020.

(51) Int. Cl.
A61K 39/145    (2006.01)
A61K 38/00     (2006.01)
A61K 39/00     (2006.01)
A61K 39/12     (2006.01)
A61P 31/16     (2006.01)
C07K 14/005    (2006.01)
C07K 14/11     (2006.01)

(52) U.S. Cl.
CPC ............ A61K 39/145 (2013.01); A61P 31/16 (2018.01); C07K 14/005 (2013.01); A61K 2039/575 (2013.01)

(58) Field of Classification Search
CPC .......... A61P 31/16; A61P 37/04; A61P 43/00; A61K 39/12; A61K 39/145
See application file for complete search history.

(56) References Cited

U.S. PATENT DOCUMENTS

| | | |
|---|---|---|
| 7,871,626 B2 | 1/2011 | Hoffmann et al. |
| 10,301,377 B2 | 5/2019 | Graham et al. |
| 10,906,944 B2 | 2/2021 | He et al. |
| 10,953,089 B1 | 3/2021 | Smith et al. |
| 10,954,289 B1 | 3/2021 | Babb et al. |
| 11,480,391 B2 | 10/2022 | Wong et al. |
| 11,866,485 B2 | 1/2024 | Lin et al. |
| 11,918,641 B2 | 3/2024 | Wong |
| 2010/0041740 A1 | 2/2010 | Wong et al. |
| 2010/0247571 A1 | 9/2010 | Wong et al. |
| 2015/0132330 A1 | 5/2015 | Garcia-Sastre et al. |
| 2016/0199481 A1 | 7/2016 | Bloom |
| 2016/0376321 A1 | 12/2016 | Hotez et al. |
| 2018/0043007 A1 | 2/2018 | LeFebvre et al. |
| 2020/0046826 A1 | 2/2020 | Wong et al. |
| 2021/0017563 A1 | 1/2021 | Bhatnagar et al. |
| 2023/0074185 A1 | 3/2023 | Wong et al. |
| 2023/0105209 A1 | 4/2023 | Lin |
| 2023/0279080 A1 | 9/2023 | Lin |
| 2023/0302114 A1 | 9/2023 | Wong |
| 2024/0016917 A1 | 1/2024 | Ma et al. |
| 2024/0066113 A1 | 2/2024 | Wong et al. |
| 2024/0100147 A1 | 3/2024 | Wong et al. |

FOREIGN PATENT DOCUMENTS

| | | |
|---|---|---|
| CN | 105934441 A | 9/2016 |
| CN | 112626124 A | 4/2021 |
| EP | 1987068 A1 | 11/2008 |
| EP | 2949665 A1 | 12/2015 |
| JP | 2017518989 A | 7/2017 |
| RU | 2720614 C1 | 5/2020 |
| RU | 2730897 C1 | 8/2020 |
| WO | 2007008918 A2 | 1/2007 |
| WO | 2007095506 A1 | 8/2007 |
| WO | 2009002516 A1 | 12/2008 |
| WO | 2009007427 A2 | 1/2009 |
| WO | 2010022737 A1 | 3/2010 |
| WO | 201011687 A2 | 9/2010 |
| WO | 2010148511 A1 | 12/2010 |
| WO | 2012054907 A2 | 4/2012 |
| WO | 2012088428 A1 | 6/2012 |
| WO | 2013043729 A1 | 3/2013 |
| WO | 2013067652 A1 | 5/2013 |

(Continued)

OTHER PUBLICATIONS

Bosch, Berend Jan et al., "Coronavirus Escape from Heptad Repeat 2 (HR2)-Derived Peptide Entry Inhibition as a Result of Mutations in the HR1 Domain of the Spike Fusion Protein," J of Virol., Mar. 2008, vol. 82, No. 5, pp. 2580-2585.

Cao, Yiwei et al., "Dynamic Interactions of Fully Glycosylated SARS-CoV-2 Spike Protein with Various Antibodies," JCTC, Sep. 16, 2021, vol. 17, pp. 6559-6569.

Castrucci, M.R et al., "Biologic importance of neuramindase stalk length in influenza A virus", Journal of Virology, 1993, vol. 67, No. 2, pp. 759-764.

Chokhawala, H.A. et al., "Enzymatic Synthesis of Fluorinated Mechanistic Proves for Sialidases and Sialyltransferases", J.Am. Chem. Soc., 2007, p. 10630; scheme 1.

(Continued)

Primary Examiner — Barry A Chestnut
(74) Attorney, Agent, or Firm — Prosyla Group PC

(57) ABSTRACT

The present disclosure relates to a chimeric influenza virus hemagglutinin (HA) polypeptide, comprising one or more stem domain sequence, each having at least 60% homology with a stem domain consensus sequence of H1 subtype HA (H1 HA) and/or H5 subtype HA (H5 HA), fused with one or more globular head domain sequence, each having at least 60% homology with a globular head domain consensus sequence of H1 subtype HA (H1 HA) or H5 subtype HA (H5 HA).

9 Claims, 17 Drawing Sheets

Specification includes a Sequence Listing.

(56) References Cited

FOREIGN PATENT DOCUMENTS

| WO | 2014115797 A1 | 7/2014 |
|---|---|---|
| WO | 2015073727 A1 | 5/2015 |
| WO | 2015184004 A1 | 12/2015 |
| WO | 2017062496 A2 | 4/2017 |
| WO | 2018089407 | 11/2017 |
| WO | 2019028190 A1 | 2/2019 |
| WO | 2015028478 A1 | 6/2019 |
| WO | 2020011275 A1 | 1/2020 |
| WO | 2020205034 | 3/2020 |
| WO | 2019246363 | 4/2020 |
| WO | 2020172072 A1 | 8/2020 |
| WO | 2020198865 A1 | 10/2020 |
| WO | 2021019102 A2 | 2/2021 |
| WO | 2021045836 A1 | 3/2021 |
| WO | 2021226533 | 5/2021 |
| WO | 2021180602 A1 | 9/2021 |
| WO | 2021183195 A1 | 9/2021 |
| WO | 2022221837 | 4/2022 |
| WO | 2022221835 A2 | 10/2022 |
| WO | 2023056482 | 10/2022 |
| WO | 2023129928 | 12/2022 |
| WO | 2023129928 A2 | 7/2023 |

OTHER PUBLICATIONS

Dang, Juanjuan et al., "Multivalency-assisted membrane-penetrating siRNA delivery sensitizes photothermal ablation via inhibition of tumor glycolysis metabolism," Biomaterials, vol. 223, Dec. 2019, 119463.

Davies, Nicholas G. et al., "Estimated transmissibility and impact of SARS-CoV-2 lineage B. 1.1.7 in England," Science, Apr. 2021, vol. 372, pp. 149 (10 pages).

Dowling, W. et al., "Influences of Glycosylation on Antigenicity, Immunogenicity, and Protective Efficacy of Ebola Virus GP DNA Vaccines", J. of Virology, 2007, vol. 81, No. 4, pp. 1821-1837, p. 1822, second col. fourth paragraph; p. 1823, second column, third paragraph; doi:10.1128/JVI.02098-06.

Edwards, et al., "The Remarkable Flexibility of the Human Antibody Repertoire; Isolation of Over One Thousand Different Antibodies to a Single Protein, BLyS," J. Mol. Biol., Nov. 2003, 14:334(1): 103-18; doi: 10.1016/jmb.2003.09.054. PMID 14596803.

Feng et al., "A Glycolipid Adjuvant, 7DW8-5, Enhances the Protective Immune Response to the Current Slpit Influenza Vaccine in Mice", Frontiers in Microbiology, Sep. 18, 2019, vol. 10, No. 2157M, pp. 1-9; abstract.

Galili, "Amplifying immunogenicity of prospective Covid-19 vaccines by glycoengineering the coronavirus glycan-shield to present alpha-gal epitopes", Vaccine, Aug. 19, 2020; abstract; Fig. 1; DOI: 10.1016/j.vaccine.2020.08032.

Galili, Uri, "Amplifying immunogenicity of prospective Covid-19 vaccines by glycoengineering the coronavirus glycan-shield to present [alpha]-gal epitopes," Vaccine, 2020, vol. 38, pp. 6487-6499.

GenBank Accession BCN86353.1 accessed on Jan. 22, 2021. https://www.ncbi.nlm.nih.gov/protein/BCN86353.1?report=genbank&log$=protalign&blast_rank=2&RID=EYKWWEAA016.

GenBank Accession CCH23214, haemagglutinin [Influenza A virus (A/WSN/1933(H1N1))], 2013.

GenBank accession MN908947.3, Mar. 18, 2020, 11 pages. (https://www.ncbi.nlm.nih.gov/nuccore/MN908947).

GenBank Accession, ACF54601, neuraminidase [Influenza A virus (A/WSN/1933(H1N1))], 2008.

GenBank: QLB39105.1 accessed on Jan. 1, 2020. https://www.ncbi.nlm.nih.gov/protein/QLB39105.1?report=genbank&log$=protalign&blast_rank=1&RID=EYKWWEAA016.

GenBank: QTA38985.1 accessed Mar. 21, 2021. https://www.ncbi.nlm.nih.gov/protein/QTA38985.1?report=genbank&log$=protalign&blast_rank=3&RID=EYKWWEAA016.

Gillian, M. Air, "Influenza neuraminidase", Influenza and Other Respiratory Viruses, 2011.

Goel, Manisha et al., "Plasticity within the Antigen-Combining Site May Manifest as Molecular Mimicry in the Humoral Immune Response," J. Immunol., Dec. 15, 2004, 173(12):7358-67 PMID: 15585860 DOI: 10.4049/jimmunol. 173.12.7358.

Hayashi, T. et al., "Stereospecific α-Sialylation by Site-Selective Fluorination", Agnew. Chem. Int. Ed., Jan. 25, 2019, vol. 58, pp. 3814-3818. (Whole Document).

Hughes et al., "Adaptation of Influenza A Viruses to Cells Expressing Low Levels of Sialic Acid Leads to Loss of Neuraminidase Activity", Journal of Virology, 2001, vol. 75, No. 8, pp. 3766-3770.

International Search Report and Written Opinion issued on Jun. 22, 2023 in International Patent Application No. PCT/US22/82428.

Janeway Jr., Charles A et al., "Immunobiology: The Immune System in Health and Disease," 3rd edition, Garland Publishing Inc., 1997, pp. 3:1-3:11.

Kanyavuz, Alexia et al., "Breaking the law: unconventional strategies for antibody diversification," Nat Rev Immunol., Jun. 2019, 19(6):355-368. doi: 10.1038/S41577-019-0126-7. PMID: 30718829.

Lescar et al., "Crystal Structure of a Cross-reaction Complex between Fab F9.13.7 and Guinea Fowl Lysozyme," J Biol Chem., Jul. 1995, 270(30):18067-76. doi: 10.1074/jbc.270.30.18067. PMID: 7629116.

Li, et al., Glycosylation of Neuraminidase Determines the Neurovirulence of Influenza A/WSN/33 Virus, 1993, Journal of Virology, vol. 67, No. 11, pp. 6667-6673.

Liu, Wen-Chun et al., "Unmasking Stem-Specific Neutralizing Epitopes by Abolishing N-Linked Glycosylation Sites of Influenza Virus Hemagglutinin Proteins for Vaccine Design", Journal of Virology, vol. 90 No. 19, Oct. 2016.

Lloyd, C. et al., "Modelling the human immune response: performance of a 10(11) human antibody repertoire against a broad panel of therapeutically relevant antigens," Protein Engineering Design & Selection, 2009, vol. 22, No. 3, pp. 159-168. doi: 10.1093/protein/gzn058.

Lo, H.-J. et al., "Synthesis of Sialidase-Resistant Oligosaccharide and Antibody Glycoform Containing α2,6-Linked 3Fax-Neu5Ac", J. Am. Chem. Soc., Apr. 10, 2019, vol. 141, No. 16, pp. 6484-6488. (Whole Document.).

Lostalé-Seijo, Irene and Montenegro, Javier, "Synthetic materials at the forefront of gene delivery," Nature Reviews Chemistry, vol. 2, Sep. 21, 2018, pp. 258-277.

Medina, Rafael A. et al., "Glycosylations in the globular head of the hemagglutinin protein modulate the virulence and antigenic properties of the H1N1 influenza viruses", Sci Transl Med., May 29, 2013.

Nobusawa et al., "Comparison of Complete Amino Acid Sequences and Receptor-Binding Properties among 13 Serotypes of Hemagglutinins of Influenza A Viruses", Virology, 182, 475-485 (1991).

Non-Final Office Action issued in U.S. Appl. No. 17/937,744 dated Jul. 5, 2023.

Office Action and Search Report issued in Taiwan Patent Application No. 111113933 on Mar. 26, 2024. English translation of search report.

Office Action issued in Taiwan Patent Application No. 111113932 on Oct. 16, 2023.

Office Action issued on Nov. 14, 2022, in Israel Patent Application No. 293502.

Official Action, dated Aug. 31, 2023, received in Russia Patent Application No. 2023100504. English translation provided.

Okamoto, K. et al., "An effective synthesis of α-glycosides of N-acetylneuraminic acid by use of 2ß-halo-3ß-hydroxy-4,7,8,9-tetra-O-acetyl-N-acetylneuraminic acid methyl ester", Tetrahedron Letters, 1986, vol. 27, No. 43, pp. 5233-5236.

Rahman, M Shaminur et al., "Epitope-based chimeric peptide vaccine design against S, M, and E proteins of SARS-CoV-2, the etiologic agent of COVID-19 pandemic, an in silico approach", PeerJ, Jul. 27, 2020 (publication date), DOI 10.7717/peerj.9572, Internal pp. 1-30, Supplemental Information pp. 1, 2. Abstract; and supplemental information pp. 1, 2.

Rees-Spear, Chloe et al., "The effect of spike mutations on SARS-CoV-2 neutralization," Cell Rep., Mar. 2023, 34 (12): 108890.

(56) References Cited

OTHER PUBLICATIONS

Published online Mar. 6, 2021. doi: 10.1016/j.celrep.2021.108890: 10.1016/j.celrep.2021.108890 PMCID: PMC7936541 PMID: 33713594.
Roberts, Paul C. et al., "Role of Conserved Glycosylation Sites in Maturation and Transport of Influenza A Virus Hemagglutinin", Journal of Virology, Jun. 1993, p. 3048-3060.
Rudikoff et al., "Single amino acid substitution altering antigen-binding specificity," Proc. Natl Acad Sci U S A, Mar. 1982, vol. 79(6), pp. 1979-1983. doi: 10.1073/pnas.79.6.1979. PC/D: 6804947.
Sanda, Miloslav et al., "N- and O-Glycosylation of the SARS-CoV-2 Spike Protein," Anal. Chem., vol. 93, No. 4, Jan. 7, 2021, pp. 2003-2009.
Search Report, dated Aug. 31, 2023, received in Russia Patent Application No. 2023100504.
Sun et al., "N-Linked Glycosylation of the Hemagglutinin Protein Influences Virulence and Antigenicity of the 1918 Pandemic and Seasonal H1N1 Influenza A Viruses", 2013, Journal of Virology, vol. 87, No. 15, pp. 8756-8766.
Tai, Wanbo et al., "Characterization of the receptor-binding domain (RBD) of 2019 novel coronavirus: implication for development of RBD protein as a viral attachment inhibitor and vaccine," Cell Mol Immunol. Jun. 2020; 17(6):613-620 https://pubmed.ncbi.nlm.nih.gov/32203189/.
Tian, Jing-Hui et al., "SARS-CoV-2 spike glycoprotein vaccine candidate NVX-CoV2373 immunogenicity in baboons and protection in mice," Nature Communications, 2021, 14 pages. Downloaded Sep. 27, 2023: https://doi.org/10.1038/s41467-020-20653-8.
Torres-Vanegas, Julian D., "Delivery Systems for Nucleic Acids and Proteins: Barriers, Cell Capture Pathways and Nanocarriers," Pharmaceutics, vol. 13, No. 3, Mar. 22, 2021, pp. 428.
Vogel, Annette B. et al. "BNT162b vaccines protect rhesus macaques from SARS-CoV-2," Nature, vol. 592, Feb. 1, 2021, pp. 283-289.
Watanabe, Yasunori et al., "Site-specific glycan analysis of the SARS-CoV-2 spike," Science, Jul. 2020, vol. 369, pp. 330-333.
Weissman, Drew et al., "D614G Spike Mutation Increases SARS COV-2 Susceptibility to Neutralization," Cell Host & Microbe, Jan. 13, 2021, vol. 29, pp. 23-31 (e1-e4).
Wu, Chung-Yi et al., "Influenza A surface glycosylation and vaccine design", PNAS, Jan. 2017, (Epub Dec. 27, 2016), vol. 114, No. 2, pp. 280-285.

Yang, Zhiwei et al., "Mutation effects of neuraminidases and their docking with ligands: a molecular dynamics and free energy calculation study", J Comput Aided Mol Des, 27: 935-950, 2013.
Zaraket, Hassan et al., "Full Genome Characterization of Human Influenza A/H3N2 Isolates from Asian Countries Reveals a Rare Amantadine Resistance-Conferring Mutation and Novel PB1-F2 Polymorphisms", Frontiers in Microbiology, vol. 7, Article 262, Mar. 2016.
Zhang, Xiaojian et al., "Role of stem glycans attached haemagglutinin in the biological characteristics of H5N1 avian influenza virus", Journal of General Virology, 96, 1248-1257, 2015.
Zhang, Yan et al., "Glycosylation on Hemagglutinin Affects the Virulence and Pathogenicity of Pandemic H1N1/2009 Influenza A Virus in Mice", Plos One, vol. 8, Issue 4, Apr. 2013.
Zhao, "Glycans of SARS-CoV-2 Spike Protein in Virus Infection and Antibody Production", Frontiers in Molecular Biosciences, Apr. 13, 2021; Entire Document; DOI: 10.3389/fmolb.2021.629873.
Zheng, J. et al., "Identification of N-linked glycosylation sites in the spike protein and their functional impact on the replication and infectivity of coronavirus infectious bronchitis virus in cell culture", Virology, Oct. 13, 2017, vol. 513, pp. 65-74; abstract; p. 65, 1st column second paragraph; p. 66, column 5th paragraph; p. 68, first column, first, third paragraphs; Table 3; figure 5; http://dx.doi.org/10.1016/j.virol.2017.10.003.
Bernstein, David et al., "Immunogenicity of chimeric haemagglutinin-based, universal influenza virus vaccine candidates: interim results of a randomized, placebo-controlled, phase 1 clinical trial", The Lancet Infectious Disease, Elsevier, Amerstdam, NL, vol. 20, No. 1, Oct. 17, 2019, pp. 80-91, XP085982810. ISSN: 1473-3099, DOI: 10.1016/S1473-3099(19)30393-7.
Focosi, Daniele, "Neutralising antibody escape of SARS-CoV-2 spike protein: Risk assessment for antibody-based Covid-19 therapeutics and vaccines," Rev. Med Virol., 2021, vol. 31, 21 pages. e2231.
GenBank Accession: QHD43416.1, (Mar. 18, 2020) [Described in the Office Action as Appendix A] (Year: 2020).
Huang et al., "Impact of glycosylation on SARS-CoV-2 infection and broadly protective vaccine design," BioRxiv, May 25, 2021, DOI: https://doi.org/10.1101/2021.05.25.445523, internal pp. 1-48.
Magazine, Nicholas et al., "Mutations and Evolution of the SARS-CoV-2 Spike Protein," Viruses, 2022, vol. 14, 640, 11 pgs.

SEQUENCE LISTING

```
Sequence total quantity: 14
SEQ ID NO: 1            moltype = AA  length = 41
FEATURE                 Location/Qualifiers
source                  1..41
                        mol_type = protein
                        organism = Influenza A virus
SEQUENCE: 1
DTLCIGYHAN NSTDTVDTVL EKNVTVTHSV NLLEDKHNGK L                     41

SEQ ID NO: 2            moltype = AA  length = 237
FEATURE                 Location/Qualifiers
source                  1..237
                        mol_type = protein
                        organism = Influenza A virus
SEQUENCE: 2
NTTCQTPKGA INTSLPFQNI HPITIGKCPK YVKSTKLRLA TGLRNVPSIQ SRGLFGAIAG   60
FIEGGWTGMV DGWYGYHHQN EQGSGYAADL KSTQNAIDKI TNKVNSVIEK MNTQFTAVGK  120
EFNHLEKRIE NLNKKVDDGF LDIWTYNAEL LVLLENERTL DYHDSNVKNL YEKVRNQLKN  180
NAKEIGNGCF EFYHKCDNTC MESVKNGTYD YPKYSEEAKL NREEIDGVKL ESTRIYQ     237
```

```
SEQ ID NO: 3                moltype = AA   length = 233
FEATURE                     Location/Qualifiers
source                      1..233
                            mol_type = protein
                            organism = Influenza A virus
SEQUENCE: 3
CDLDGVKPLI LRDCSVAGWL LGNPMCDEFI NVPEWSYIVE KANPANDLCY PGNFNDYEEL     60
KHLLSRINHF EKIQIIPKSS WSDHEASSGV SSACPYQGKS SFFRNVVWLI KKNSTYPTIK    120
RSYNNTNQED LLVLWGIHHP NDAAEQTRLY QNPTTYISVG TSTLNQRLVP KIATRSKVNG    180
QSGRMEFFWT ILKPNDAINF ESNGNFIAPE YAYKIVKKGD STIMKSELEY GNC           233

SEQ ID NO: 4                moltype = AA   length = 511
FEATURE                     Location/Qualifiers
REGION                      1..511
                            note = chimeric influenza virus HA polypeptide
source                      1..511
                            mol_type = protein
                            organism = synthetic construct
SEQUENCE: 4
DTLCIGYHAN NSTDTVDTVL EKNVTVTHSV NLLEDKHNGK LCDLDGVKPL ILRDCSVAGW     60
LLGNPMCDEF INVPEWSYIV EKANPANDLC YPGNFNDYEE LKHLLSRINH FEKIQIIPKS    120
SWSDHEASSG VSSACPYQGK SSFFRNVVWL IKKNSTYPTI KRSYNNTNQE DLLVLWGIHH    180
PNDAAEQTRL YQNPTTYISV GTSTLNQRLV PKIATRSKVN GQSGRMEFFW TILKPNDAIN    240
FESNGNFIAP EYAYKIVKKG DSTIMKSELE YGNCNTTCQT PKGAINTSLP FQNIHPITIG    300
KCPKYVKSTK LRLATGLRNV PSIQSRGLFG AIAGFIEGGW TGMVDGWYGY HHQNEQGSGY    360
AADLKSTQNA IDKITNKVNS VIEKMNTQFT AVGKEFNNLE KRIENLNKKV DDGFLDIWTY    420
NAELLVLLEN ERTLDYHDSN VKNLYEKVRN QLKNNAKEIG NGCFEFYHKC DNTCMESVKN    480
GTYDYPKYSE EAKLNREEID GVKLESTRIY Q                                   511

SEQ ID NO: 5                moltype = AA   length = 41
FEATURE                     Location/Qualifiers
source                      1..41
                            mol_type = protein
                            organism = Influenza A virus
SEQUENCE: 5
DTLCIGYHAN NSTDTVDTVL EKNVTVTHSV NLLEDKHNGK L                          41

SEQ ID NO: 6                moltype = AA   length = 228
FEATURE                     Location/Qualifiers
REGION                      1..228
                            note = stem domain consensus sequence of H1 HA and H5 HA
source                      1..228
                            mol_type = protein
                            organism = synthetic construct
SEQUENCE: 6
NTTCQTPKGA INTSLPFQNI HPITIGKCPK YVKSTKLRLA TGLRNVPSIQ SRGLFGAIAG     60
FIEGGWQGMV DGWYGYHHSN EQGSGYAADK ESTQKAIDGV TNKVNSIIDK MNTQFEAVGR    120
EFNNLERRIE NLNKKMEDGF LDVWTYNAEL LVLMENERTL DFHDSNVKNL YDKVRLQLRD    180
NAKELGNGCF EFYHKCDNEC MESVRNGTYD YPQYSEEARL KREEISGV                 228

SEQ ID NO: 7                moltype = AA   length = 234
FEATURE                     Location/Qualifiers
source                      1..234
                            mol_type = protein
                            organism = Influenza A virus
SEQUENCE: 7
CKLRGVAPLH LGKCNIAGWI LGNPECESLS TASSWSYIVE TSSSDNGTCY PGDFIDYEEL     60
REQLSSVSSF ERFEIFPKTS SWPNHDSNKG VTAACPHAGA KSFYKNLIWL VKKGNSYPKL    120
SKSYINDKGK EVLVLWGIHH PSTTADQQSL YQNADAYVFV GTSRYSKKFK PEIAIRPKVR    180
DQEGRMNYYW TLVEPGDKIT FEATGNLVVP RYAFAMERNA GSGIIISDTP VHDC           234

SEQ ID NO: 8                moltype = AA   length = 503
FEATURE                     Location/Qualifiers
REGION                      1..503
                            note = chimeric influenza virus HA polypeptide
source                      1..503
                            mol_type = protein
                            organism = synthetic construct
SEQUENCE: 8
DTLCIGYHAN NSTDTVDTVL EKNVTVTHSV NLLEDKHNGK LCKLRGVAPL HLGKCNIAGW     60
ILGNPECESL STASSWSYIV ETSSSDNGTC YPGDFIDYEE LREQLSSVSS FERFEIFPKT    120
SSWPNHDSNK GVTAACPHAG AKSFYKNLIW LVKKGNSYPK LSKSYINDKG KEVLVLWGIH    180
HPSTTADQQS LYQNADAYVF VGTSRYSKKF KPEIAIRPKV RDQEGRMNYY WTLVEPGDKI    240
TFEATGNLVV PRYAFAMERN AGSGIIISDT PVHDCNTTCQ TPKGAINTSL PFQNIHPITI    300
GKCPKYVKST KLRLATGLRN VPSIQSRGLF GAIAGFIEGG WQGMVDGWYG YHHSNEQGSG    360
YAADKESTQK AIDGVTNKVN SIIDKMNTQF EAVGREFNNL ERRIENLNKK MEDGFLDVWT    420
YNAELLVLME NERTLDFHDS NVKNLYDKVR LQLRDNAKEL GNGCFEFYHK CDNECMESVR    480
NGTYDYPQYS EEARLKREEI SGV                                            503
```

```
SEQ ID NO: 9           moltype = AA   length = 41
FEATURE                Location/Qualifiers
source                 1..41
                       mol_type = protein
                       organism = Influenza A virus
SEQUENCE: 9
DQICIGYHAN NSTEQVDTIM EKNVTVTHAQ DILEKTHNGK L                                41

SEQ ID NO: 10          moltype = AA   length = 232
FEATURE                Location/Qualifiers
REGION                 1..232
                       note = stem domain consensus sequence of H1 HA and H5 HA
source                 1..232
                       mol_type = protein
                       organism = synthetic construct
SEQUENCE: 10
NTKCQTPMGA INSSMPFHNI HPLTIGECPK YVKSNRLVLA TGLRNSPQRE RRRKKRGLFG      60
AIAGFIEGGW TGMVDGWYGY HHQNEQGSGY AADLKSTQNA IDKITNKVNS VIEKMNTQFT     120
AVGKEFNHLE KRIENLNKKV DDGFLDIWTY NAELLVLLEN ERTLDYHDSN VKNLYEKVRN     180
QLKNNAKEIG NGCFEFYHKC DNTCMESVKN GTYDYPKYSE EAKLNREEID GV             232

SEQ ID NO: 11          moltype = AA   length = 233
FEATURE                Location/Qualifiers
source                 1..233
                       mol_type = protein
                       organism = Influenza A virus
SEQUENCE: 11
CDLDGVKPLI LRDCSVAGWL LGNPMCDEFI NVPEWSYIVE KANPANDLCY PGNFNDYEEL      60
KHLLSRINHF EKIQIIPKSS WSDHEASSGV SSACPYQGKS SFFRNVVWLI KKNSTYPTIK     120
RSYNNTNQED LLVLWGIHHP NDAAEQTRLY QNPTTYISVG TSTLNQRLVP KIATRSKVNG     180
QSGRMEFFWT ILKPNDAINF ESNGNFIAPE YAYKIVKKGD STIMKSELEY GNC             233

SEQ ID NO: 12          moltype = AA   length = 506
FEATURE                Location/Qualifiers
REGION                 1..506
                       note = chimeric influenza virus HA polypeptide
source                 1..506
                       mol_type = protein
                       organism = synthetic construct
SEQUENCE: 12
DQICIGYHAN NSTEQVDTIM EKNVTVTHAQ DILEKTHNGK LCDLDGVKPL ILRDCSVAGW      60
LLGNPMCDEF INVPEWSYIV EKANPANDLC YPGNFNDYEE LKHLLSRINH FEKIQIIPKS     120
SWSDHEASSG VSSACPYQGK SSFFRNVVWL IKKNSTYPTI KRSYNNTNQE DLLVLWGIHH     180
PNDAAEQTRL YQNPTTYISV GTSTLNQRLV PKIATRSKVN GQSGRMEFFW TILKPNDAIN     240
FESNGNFIAP EYAYKIVKKG DSTIMKSELE YGNCNTKCQT PMGAINSSMP FHNIHPLTIG     300
ECPKYVKSNR LVLATGLRNS PQRERRRKKR GLFGAIAGFI EGGWTGMVDG WYGYHHQNEQ     360
GSGYAADLKS TQNAIDKITN KVNSVIEKMN TQFTAVGKEF NHLEKRIENL NKKVDDGFLD     420
IWTYNAELLV LLENERTLDY HDSNVKNLYE KVRNQLKNNA KEIGNGCFEF YHKCDNTCME     480
SVKNGTYDYP KYSEEAKLNR EEIDGV                                          506

SEQ ID NO: 13          moltype = AA   length = 16
FEATURE                Location/Qualifiers
REGION                 1..16
                       note = signal peptide
source                 1..16
                       mol_type = protein
                       organism = synthetic construct
SEQUENCE: 13
MEKIVLLLAI VSLVKS                                                      16

SEQ ID NO: 14          moltype = AA   length = 17
FEATURE                Location/Qualifiers
REGION                 1..17
                       note = signal peptide
source                 1..17
                       mol_type = protein
                       organism = synthetic construct
SEQUENCE: 14
MKAILVVLLY TFATANA                                                     17
```

CHIMERIC INFLUENZA VACCINES

CROSS REFERENCE TO RELATED APPLICATIONS

This application is a continuation of U.S. patent application Ser. No. 18/501,578, filed Nov. 3, 2023, which is a continuation of U.S. patent application Ser. No. 17/998,208, filed Nov. 8, 2022, which is a 371 National Phase of International Patent Application No. PCT/US21/31406, filed May 7, 2021, which claims priority to U.S. Provisional Application Ser. No. 63/022,328, filed May 8, 2020, all of which are incorporated by reference herein in their entirety for all purposes.

SEQUENCE LISTING

The subject application contains a Sequence Listing which has been filed electronically in XML format and is hereby incorporated by reference in its entirety. Said XML copy, created on May 13, 2024, is named A1000-00600C2_20240513_SeqListing.xml and is 19 kilobytes in size.

FIELD OF THE INVENTION

The present disclosure relates to a chimeric influenza virus hemagglutinin (HA) polypeptide, an immunogenic/vaccine composition containing the same and applications thereof.

BACKGROUND OF THE INVENTION

The traditional method for influenza vaccine production is to culture the virus in specific-pathogen-free (SPF) embryonated hens eggs, and the process often requires more than six months for mass production. However, some vaccine virus strains grow poorly in eggs, and people with allergy to chicken egg could cause safety concerns. New approaches based on cell culturing of viruses have been developed to replace the egg-based method; but the cell-culture method still has a risk of producing potentially hazardous viruses. To overcome these problems, exploration of alternative strategies has demonstrated that recombinant HA-based vaccines can induce neutralizing antibodies against influenza virus infection. However, the antibodies induced by a specific influenza virus subtype usually could not effectively neutralize other influenza subtypes. In addition, the vaccine has to be updated annually because of the constant mutation of the virus.

Therefore, there is still a need to develop a universal vaccine against a wide spectrum of influenza virus strains.

SUMMARY OF THE INVENTION

In one aspect, the present disclosure provides a chimeric influenza virus hemagglutinin (HA) polypeptide, comprising one or more stem domain sequence, each having at least 60% homology with a stem domain consensus sequence of H1 subtype HA (H1 HA) and/or H5 subtype HA (H5 HA), fused with one or more globular head domain sequence, each having at least 60% homology with a globular head domain consensus sequence of H1 subtype HA (H1 HA) or H5 subtype HA (H5 HA).

In some embodiments, the HA is an influenza A HA, an influenza B HA, or an influenza C HA.

In some embodiments, the homology is at least 65%, 70%, 75%, 80%, 85%, 90%, 95%, 96%, 97%, 98%, 99% or 100%.

In some embodiments, the stem domain sequence is an N-terminal stem segment of H1 HA or a C-terminal stem segment of H1 HA; an N-terminal stem segment of H1 HA or a C-terminal stem segment of H1+H5 HA sequences; or an N-terminal stem segment of H5 HA or a C-terminal stem segment of H1+H5 HA sequences.

In some embodiments, the stem domain consensus sequence of H1 HA and/or H5 HA comprises an amino acid sequence of SEQ ID NO: 1, SEQ ID NO: 2, SEQ ID NO: 5, SEQ ID NO: 6, SEQ ID NO: 9, or SEQ ID NO: 10.

In some embodiments, the globular head domain consensus sequence of H1 HA or H5 HA comprises an amino acid sequence of SEQ ID NO: 3, SEQ ID NO: 7, or SEQ ID NO: 11.

In one embodiment, the chimeric influenza virus HA polypeptide comprises an amino acid sequence of SEQ ID NO: 4, SEQ ID NO: 8, or SEQ ID NO: 12.

In some embodiments, one or more glycosites on HA are monoglycosylated. In a further embodiment, the monoglycosylated HA has only N-Acetylglucosamine (GlcNAc) on each glycosite.

In an embodiment, the chimeric influenza virus HA polypeptide is used as an immunogen.

In another aspect, the present disclosure provides an immunogenic composition comprising a chimeric influenza virus HA polypeptide and an adjuvant. In an embodiment, the adjuvant is a glycolipid adjuvant.

In another aspect, the present disclosure provides a recombinant polynucleotide comprising a nucleic acid sequence encoding a polypeptide of the present disclosure and optionally a nucleic acid sequence encoding a signal peptide. In some embodiments, the signal peptide comprises a sequence of SEQ ID NO: 13 or SEQ ID NO: 14.

In another aspect, the present disclosure provides a vector comprising a recombinant polynucleotide of the present disclosure. Also provided is a host cell which comprises a vector of the present disclosure.

In another aspect, the present disclosure provides a method of immunizing a subject against influenza virus comprising administering an effective amount of a chimeric influenza virus hemagglutinin (HA) polypeptide or an immunogenic composition of the present disclosure to the subject.

In another aspect, the present disclosure provides a method of preventing an influenza virus disease in a subject, comprising administering an effective amount of a chimeric influenza virus hemagglutinin (HA) polypeptide or an immunogenic composition of the present disclosure to the subject.

In one embodiment, the methods described herein elicit CD4$^+$ and/or CD8$^+$ T-cell immune responses.

In one embodiment, the methods described herein induce stem-specific antibodies, with higher antibody-dependent cellular cytotoxicity (ADCC), better neutralizing and stronger cross-protection activities against H1, H3, H5 and H7 strains and subtypes.

In one embodiment, the methods described herein enhance the vaccine efficacy with more IFN-γ, IL-4 and CD8+ memory T cells produced.

and broadly cross-protective, stem-specific antibodies elicited by vaccination with cHA$_{mg}$ immunogens. (A) The constructs of swap H1/5 (H1 globular head and H1+H5 [HA2] stem), swap H5/1 (H5 globular head and H5+H1 [HA2] stem) and chimeric H5/1 (cHA: H5 globular head and H1 stem). (B) Neutralization activity against H1N1 California/07/2009 and H5N1 Vietnam/1194/2004 viruses. (C) The number of granzyme B (GrzB) producing CD8+ T cells in splenocytes stimulated with HA (black bar) or PBS (white bar) control for 2 days in mice vaccinated with PBS (control), HA+Alu, or HA+C34 was evaluated by flow cytometric analysis. (D-I) The antibody titers from the mice vaccinated with cHA$_{fg}$ and cHA$_{mg}$ adjuvanted with Al(OH)$_3$ vs. cHA$_{fg}$ and cHA$_{mg}$ adjuvanted with C34 were measured on day 42 by ELISA with the A/California/07/2009 H1N1 HA protein (D), A/Brisbane/59/2007 H1N1 HA protein (E), A/Brisbane/10/2007 H3N2 HA protein (F), A/Vietnam/1194/2004 H5N1 HA protein (G), A/Shanghai/2/2013 H7N9 HA protein (H) and the A/Brisbane/59/2007 (Bris/07) stem HA (no. 4900) protein (I) as the coating antigen. The endpoint antibody titer was defined as the last dilution of antisera to produce an absorbance 2.5 times higher than the optical absorbance produced by the negative control (pre-immune serum). Data were examined by using Student's i test and two-way ANOVA from Prism; differences were considered statistically significant at *P<0.05; **P<0.01. Data represent the mean±SEM.

Figure 2:
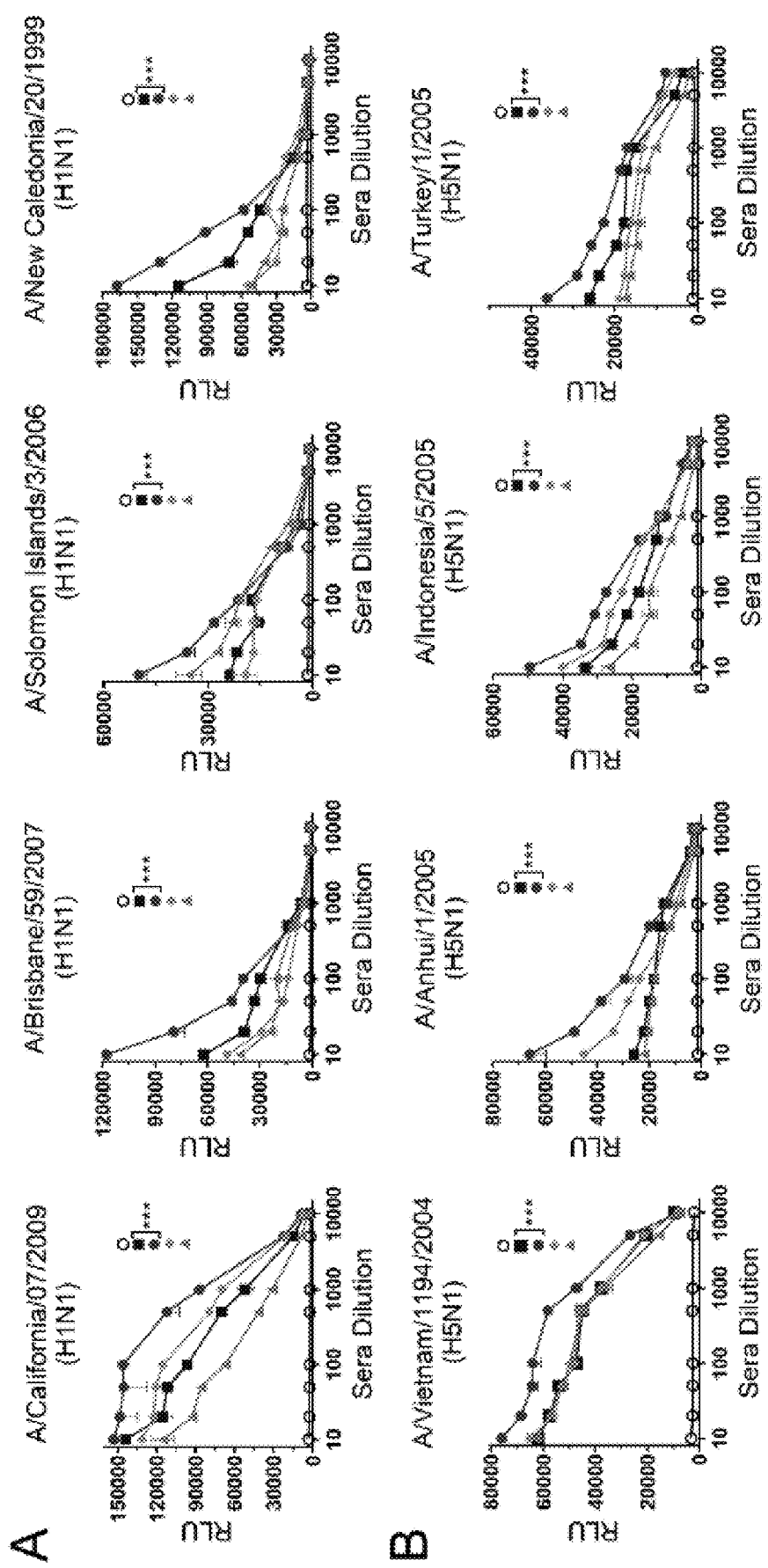
Figure 2:
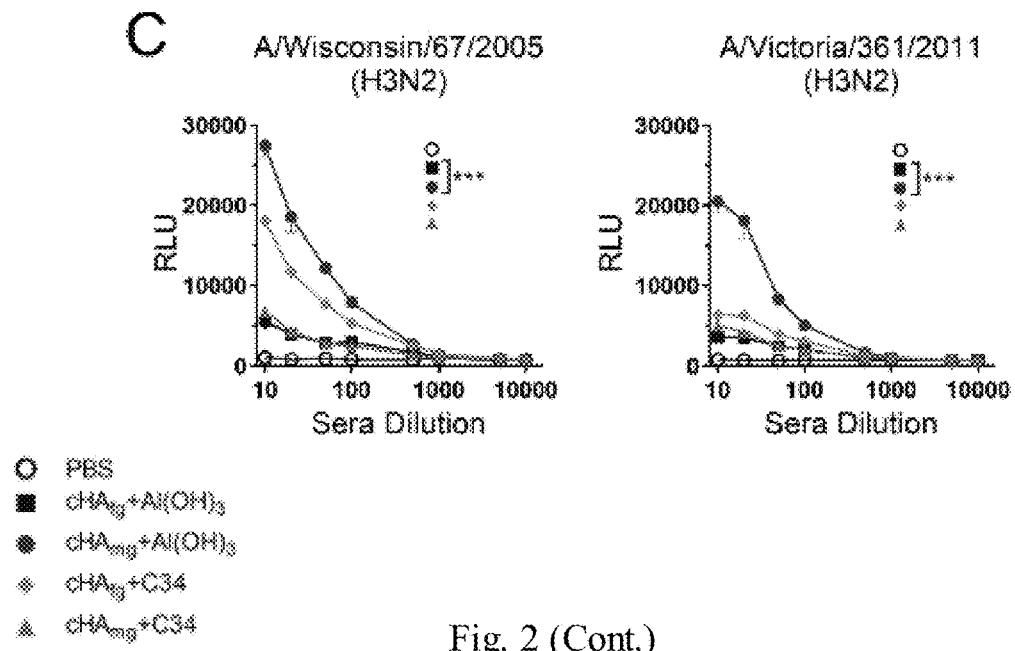

FIGS. 2 (A) to (C). ADCC reporter assay of antisera from cHA-vaccinated mice against target cells expressing the HA of H1N1, H3N2 or H5N1 and subtypes. The antisera collected from mice immunized with cHA$_{fg}$ or cHA$_{mg}$ proteins adjuvanted with aluminum hydroxide or C34 were incubated with MDCK cells which were infected with (A) H1N1 virus (B) H5N1 virus, or (C) H3N2 virus for 30 min. Subsequently, the ADCC reporter assay was performed using Jurkat effector cells expressing mouse FcγRIII and the relative luminescence unit (RLU) was measured and values are mean±SEM. ***P<0.001. The P value was calculated with Prism software using two-way ANOVAs.

Figure 3:
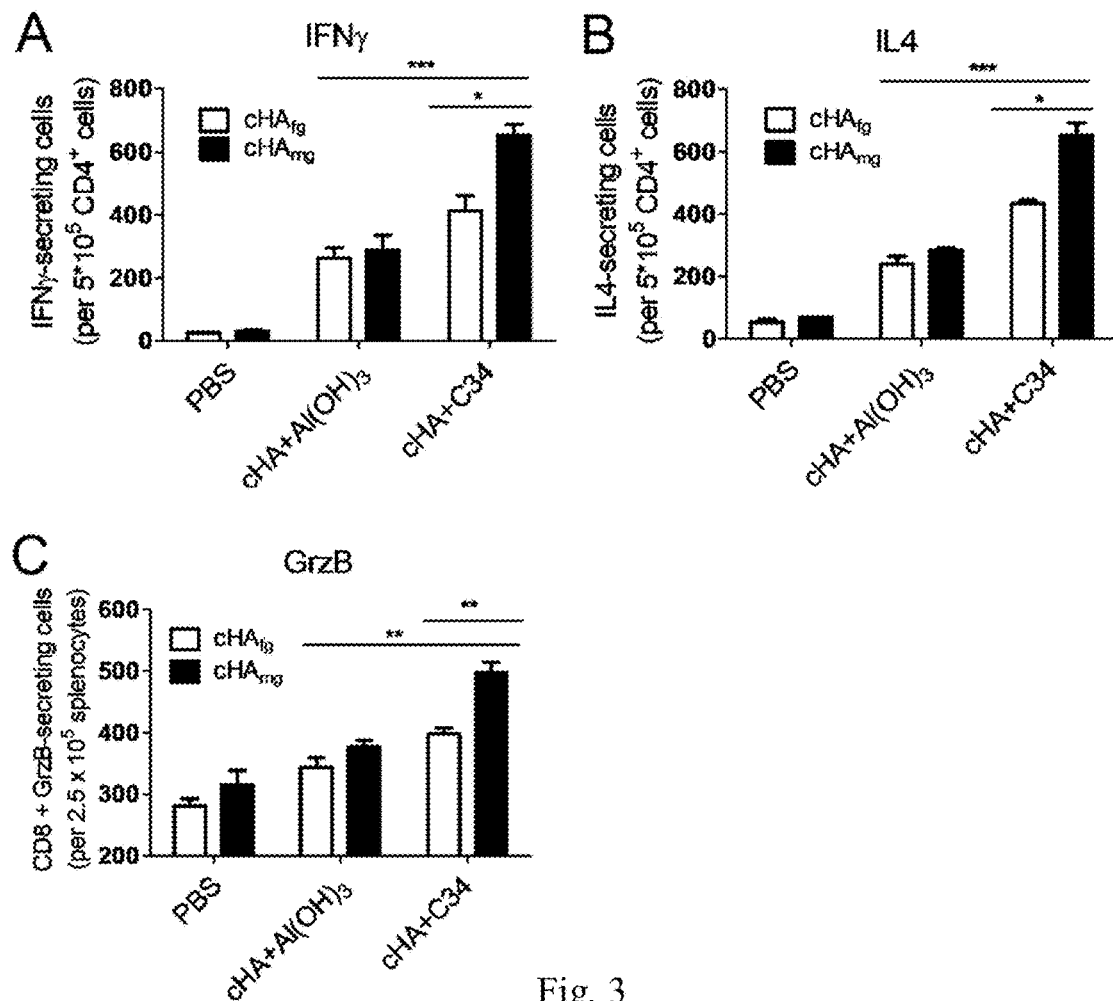
Figure 3:
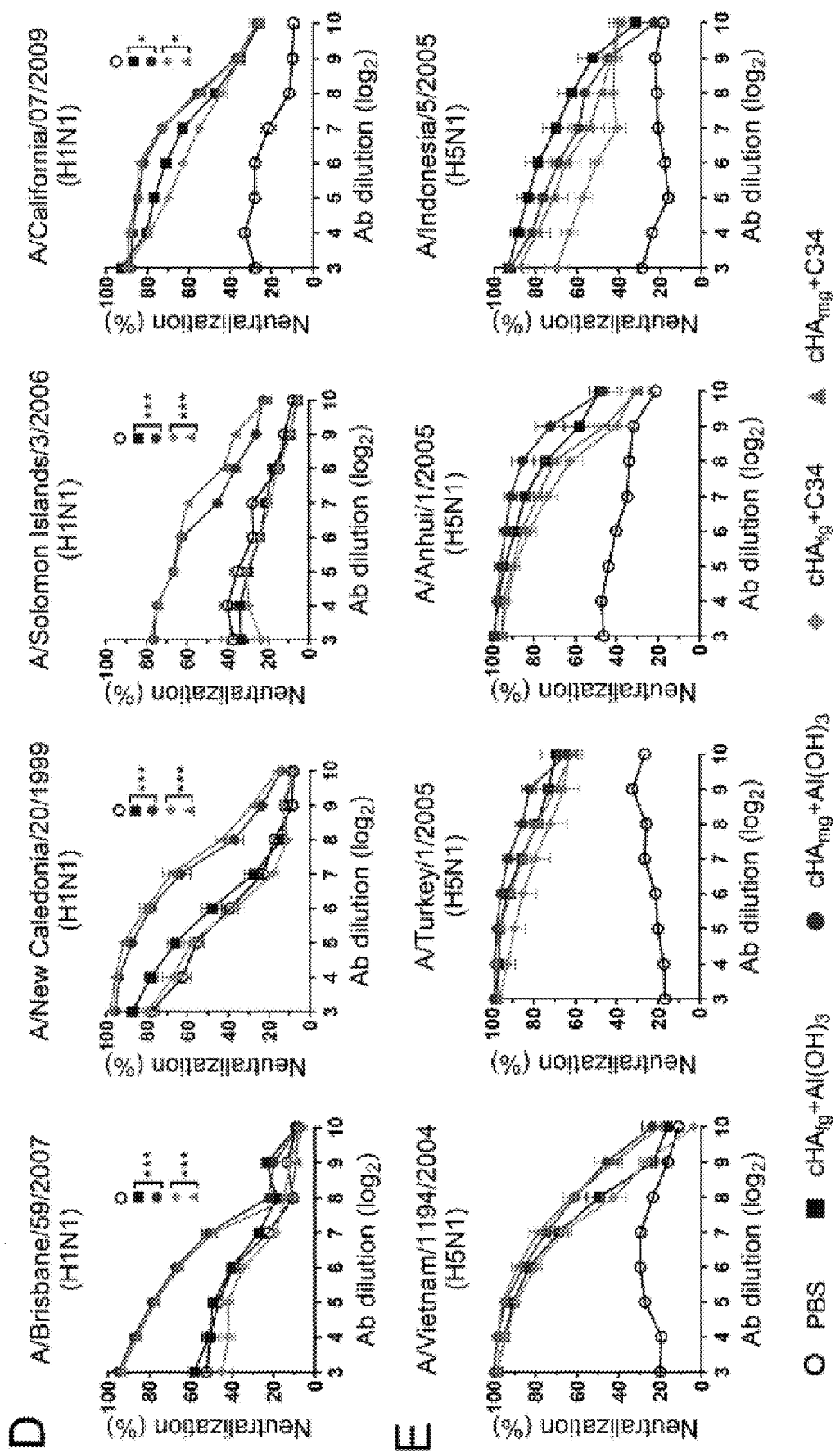

FIGS. 3 (A) to (E). More CD4+ and CD8+ T-cell responses and broadly neutralizing antibodies were elicited to give broader cross-protection by cHA$_{mg}$ with adjuvant C34. BALB/c mice were immunized with cHA$_{fg}$ and cHA$_{mg}$ with adjuvant Al(OH)$_3$ or C34; cells from spleens of immunized mice were obtained after three immunizations and the IFN-γ (A), IL-4 (B) and GzB (C)-secreting cells were determined by ELISpot assay using specific peptides. The number of spot-forming cells (SFCs) is expressed as mean±SEM. The neutralization activities of antisera from cHA$_{fg}$ and cHA$_{mg}$ vaccinated mice were assayed against (D) H1N1 virus, and (E) H5N1 virus. Data are presented as mean±SEM. Results were calculated with Prism software using Student's t test and two-way ANOVA; significant differences were marked as *P<0.05; P<0.01; *P<0.001.

Figure 4:
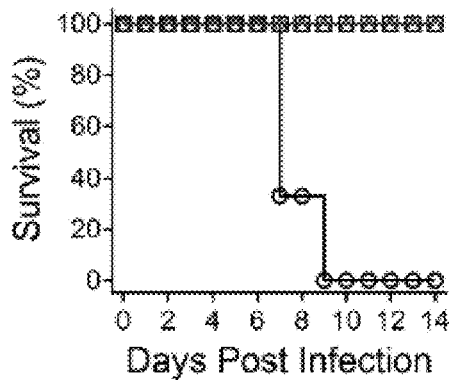
Figure 4:
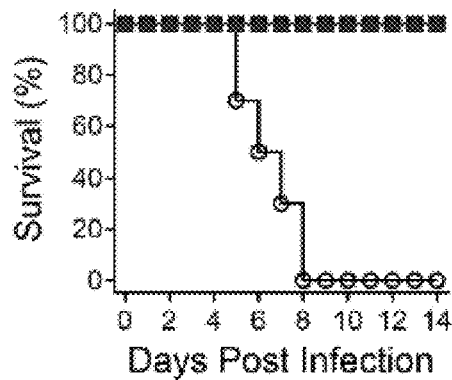
Figure 4:
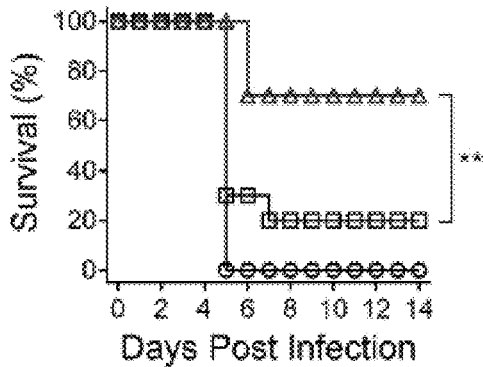
Figure 4:
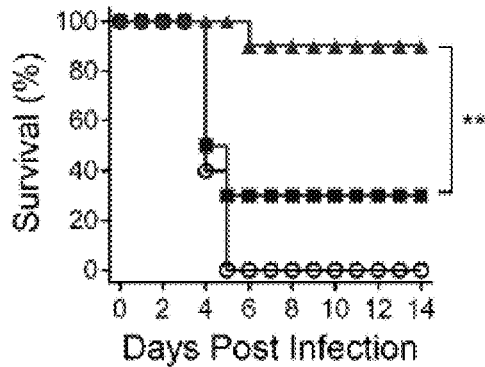
Figure 4:
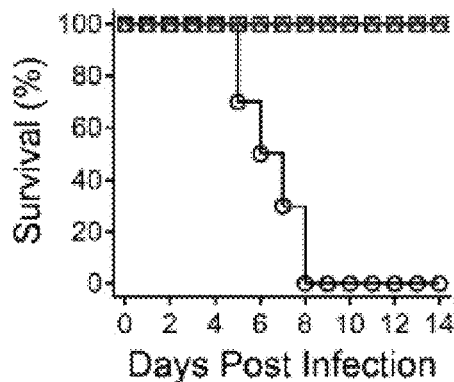
Figure 4:
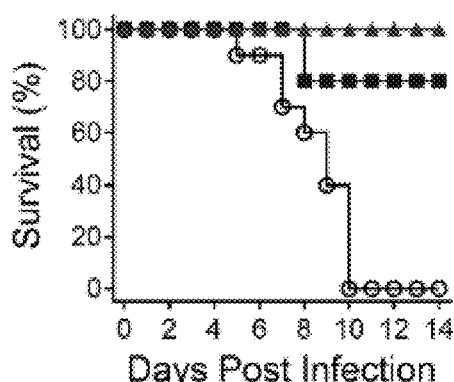
Figure 4:
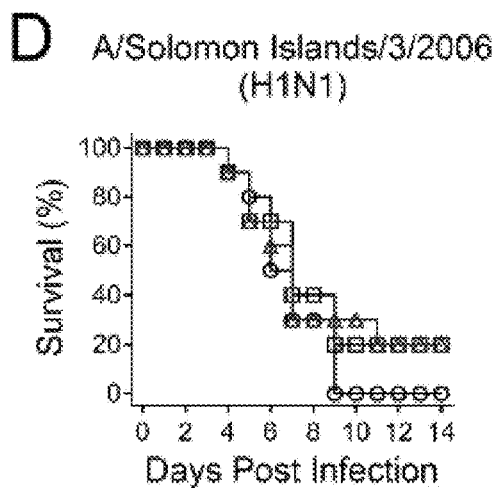
Figure 4:
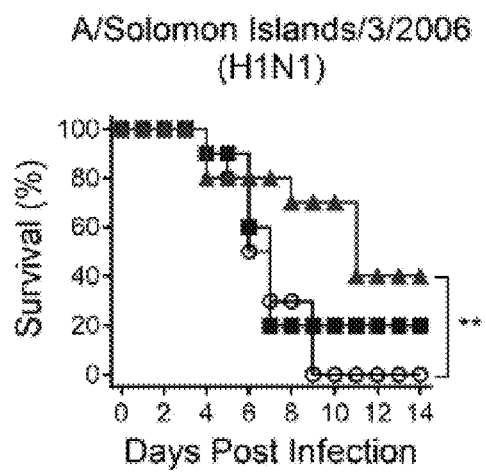
Figure 4:
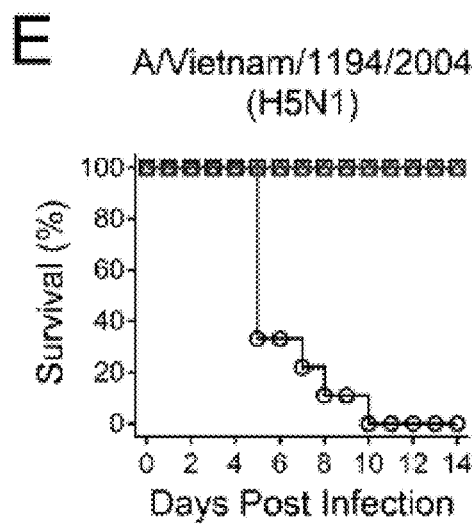
Figure 4:
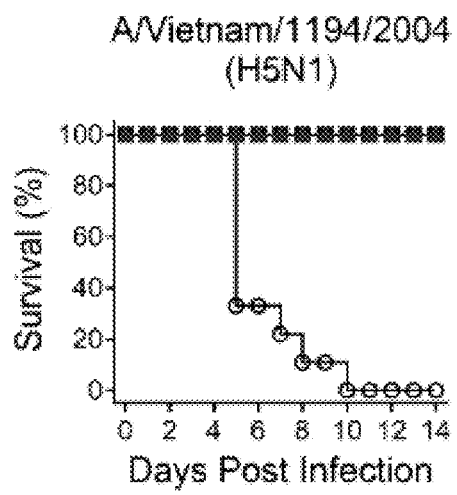
Figure 4:
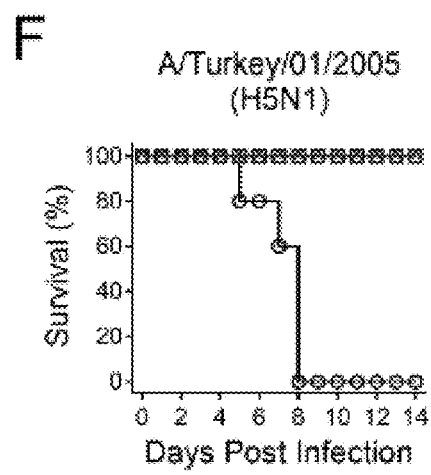
Figure 4:
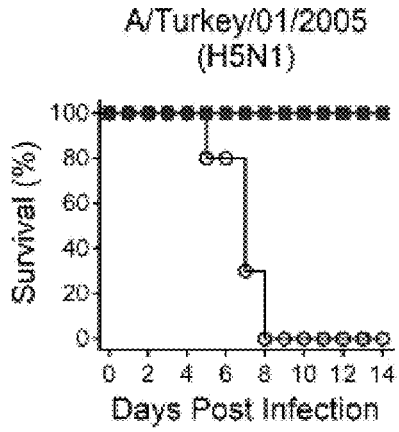

FIGS. 4 (A) to (F). Cross-protective efficacy in mice challenged with lethal doses of H1N1 and H5N1 viruses. BALB/c mice were immunized with three doses of cHA$_{fg}$ and cHA$_{mg}$ with adjuvant Al(OH)$_3$ or C34 at 2-week intervals. The immunized mice were challenged with H1N1 A/California/07/2009 (A), H1N1 A/New Caledonia/1999 (B), H1N1 A/WSN/1933 (C) H1N1 A/Solomon Islands/03/2006 (D) H5N1 A/Vietnam/1194/2004/NIBRG14 (E), or H5N1 A/Turkey/1/2005/NIBRG23 (F), and the efficacy was evaluated by recording the survival rate for 14 days after infection. **P<0.01. Significant differences in survival rate were analyzed by log-rank (Mantel-Cox) test.

Figure 5:
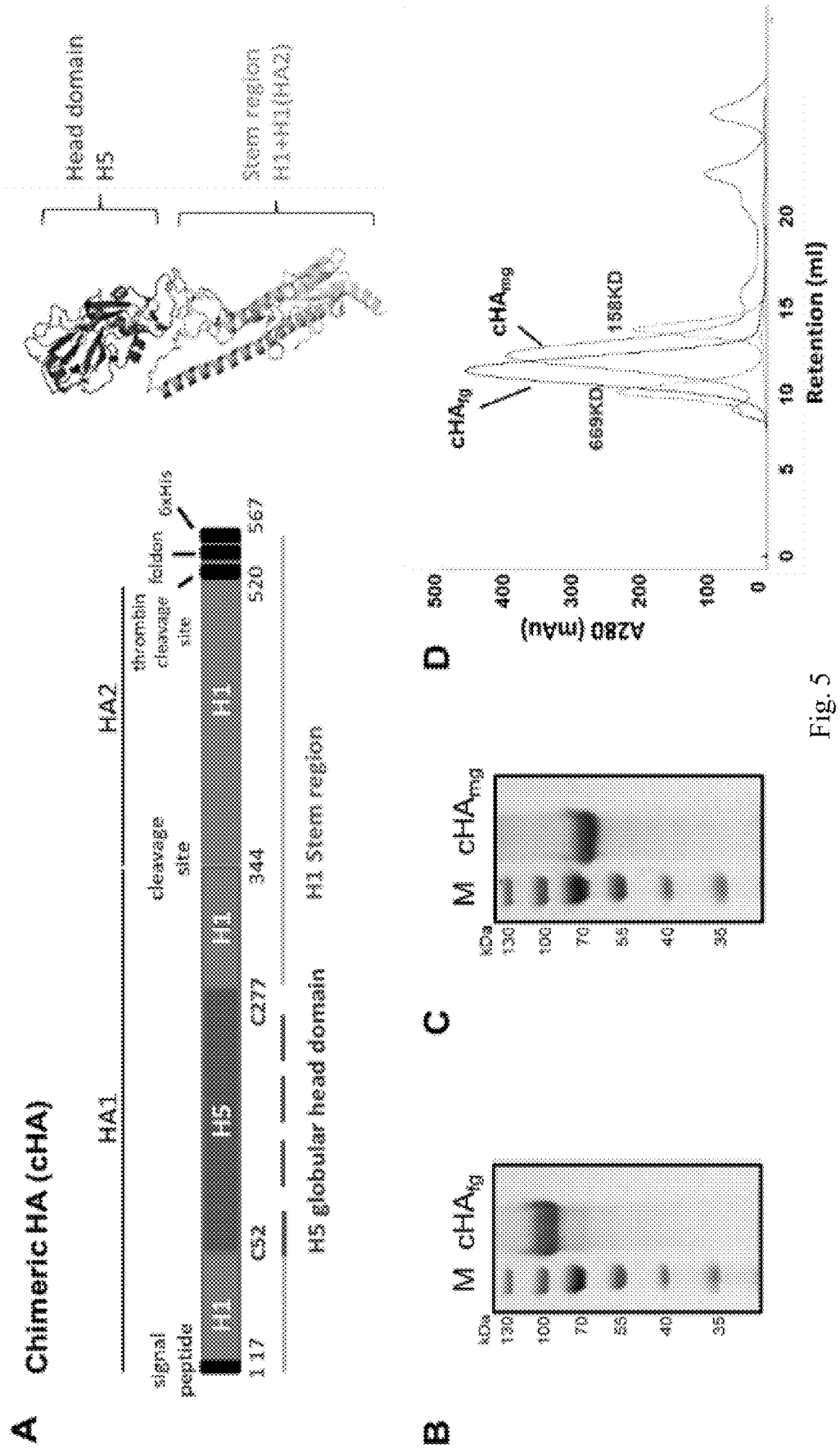
Figure 5:
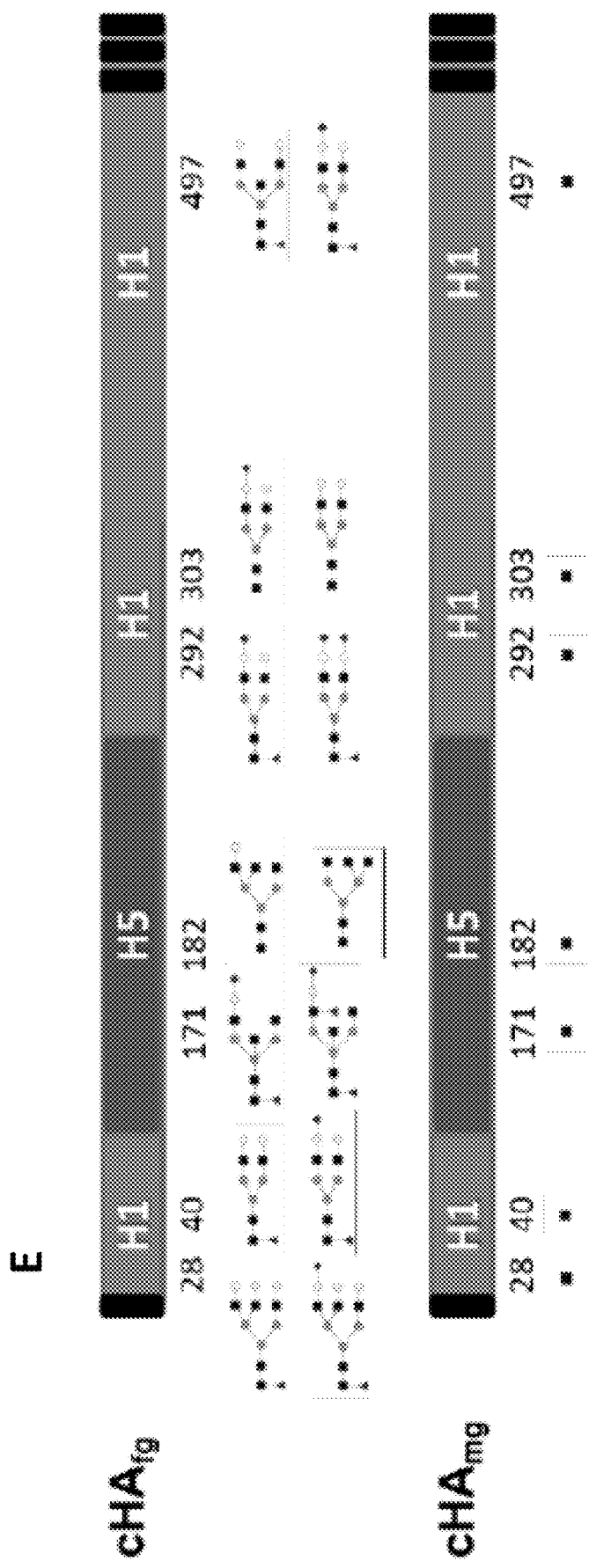

FIGS. 5 (A) to (E). Design and preparation of chimeric HA proteins. (A) The designed influenza HA sequences were constructed using the consensus H1N1 sequence and the consensus H5N1 sequence pCHA5-II to generate the chimeric HA. The globular head domain is composed of the amino acid sequence between residues C52 and C277 (H3 numbering). The stem region is composed of portions of HA1 and HA2 subunits. The protein structures were downloaded from the Protein Data Bank ID code 2IBX (VN1194 H5 HA) and 3LZG (A/California/04/2009). Final images were generated with PyMol. Because no structure of a consensus HA has been published, the image of the head domain of the avian flu H5 (Vietnam/1194/2004) and the stem region of the pandemic H1N1 (California/07/2009) are used for the chimeric HA construct. (B-D) Purification of chimeric HA protein and gel-filtration chromatography analysis. (B) The purified HA proteins were analyzed by SDS/PAGE. M: molecular weight marker. left: cHA$_{fg}$, the fully glycosylated cHA directly purified from HEK293T cells; (C) cHA$_{mg}$, the monoglycosylated cHA purified from HEK293S cells and digested with endoglycosidase H. (D) Gel filtration analysis of purified secreted HA proteins. The fully glycosylated cHA from HEK293T cells and the monoglycosylated cHA existed as a trimer (>200 kDa) as shown in chromatograph. The figure represents superimposed elution profiles of HEK293T cell-expressed cHA proteins overlaid with calibration standards (dotted line). (E) A schematic figure to mark the main glycans on the glycosites of cHA$_{fg}$ and cHA$_{mg}$ determined by LC-MS/MS. The general glycan symbols were followed.

Figure 6:
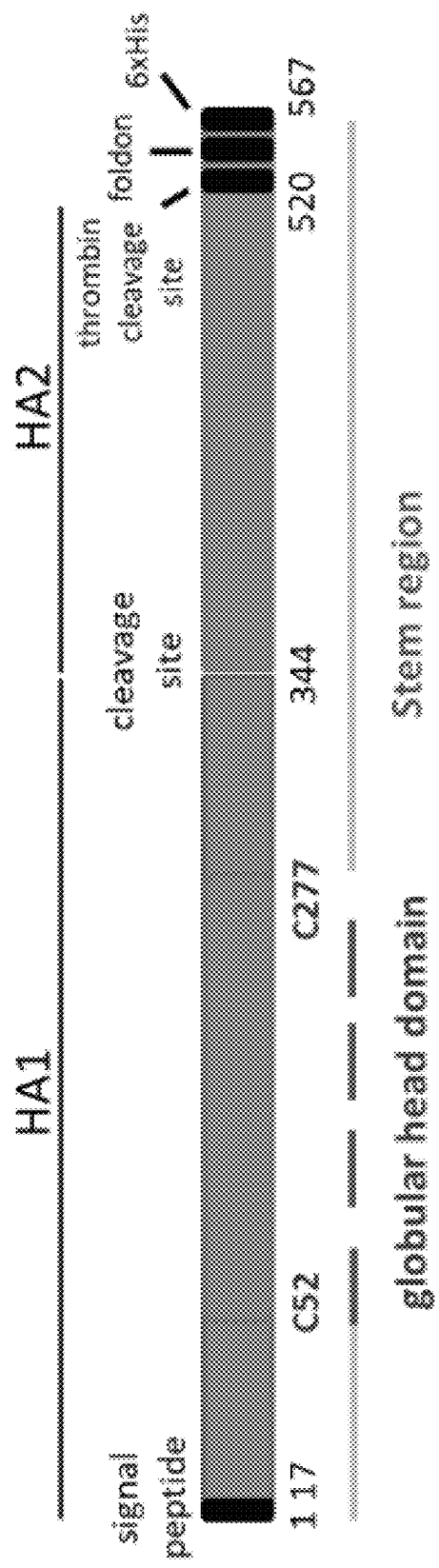
Figure 6:
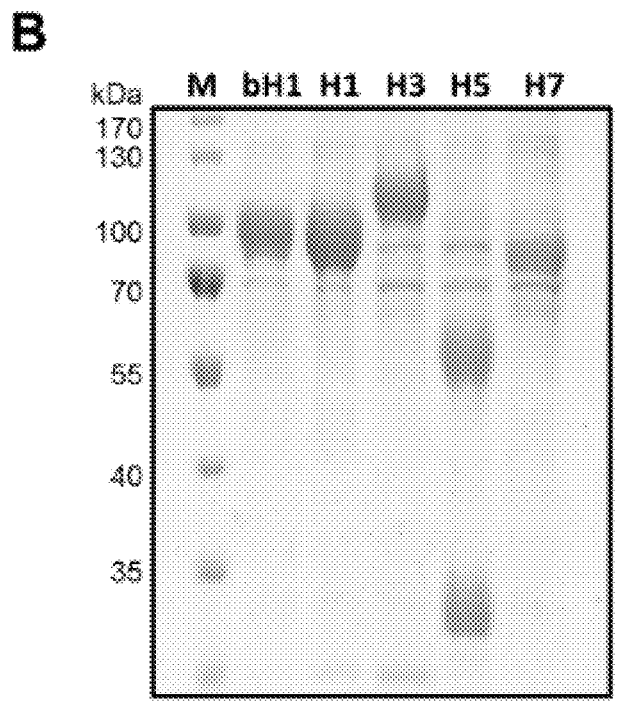

FIGS. 6 (A) and (B). The constructs of secreted HA and purification. (A) The sequence encoding the ectodomain of HA was prepared in the expression vector pcDNA and transfected to HEK293T cells. The protein was engineered to contain a stabilization/trimerization signal, foldon, as well as a C-terminal (His)$_6$ tag for purification. (B) The purified HA proteins were analyzed by SDS/PAGE. M: molecular weight marker. Lane 1: H1N1 (A/Brisbane/59/2007) HA protein; lane 2: H1N1 (A/California/07/2009) HA protein; lane 3: H3N2 (Brisbane/10/2007) HA protein; lane 4: H5N1 (Vietnam/1194/2004) HA protein; lane 5: H7N9 (A/Shanghai/2/2013) HA protein.

Figure 7:
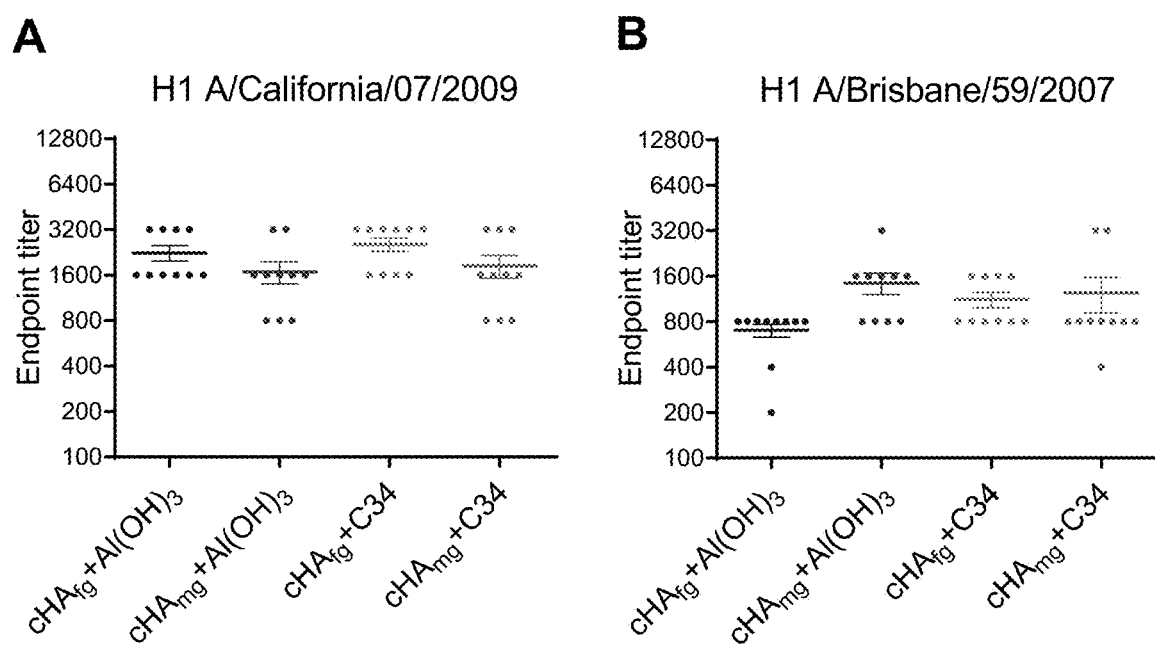
Figure 7:
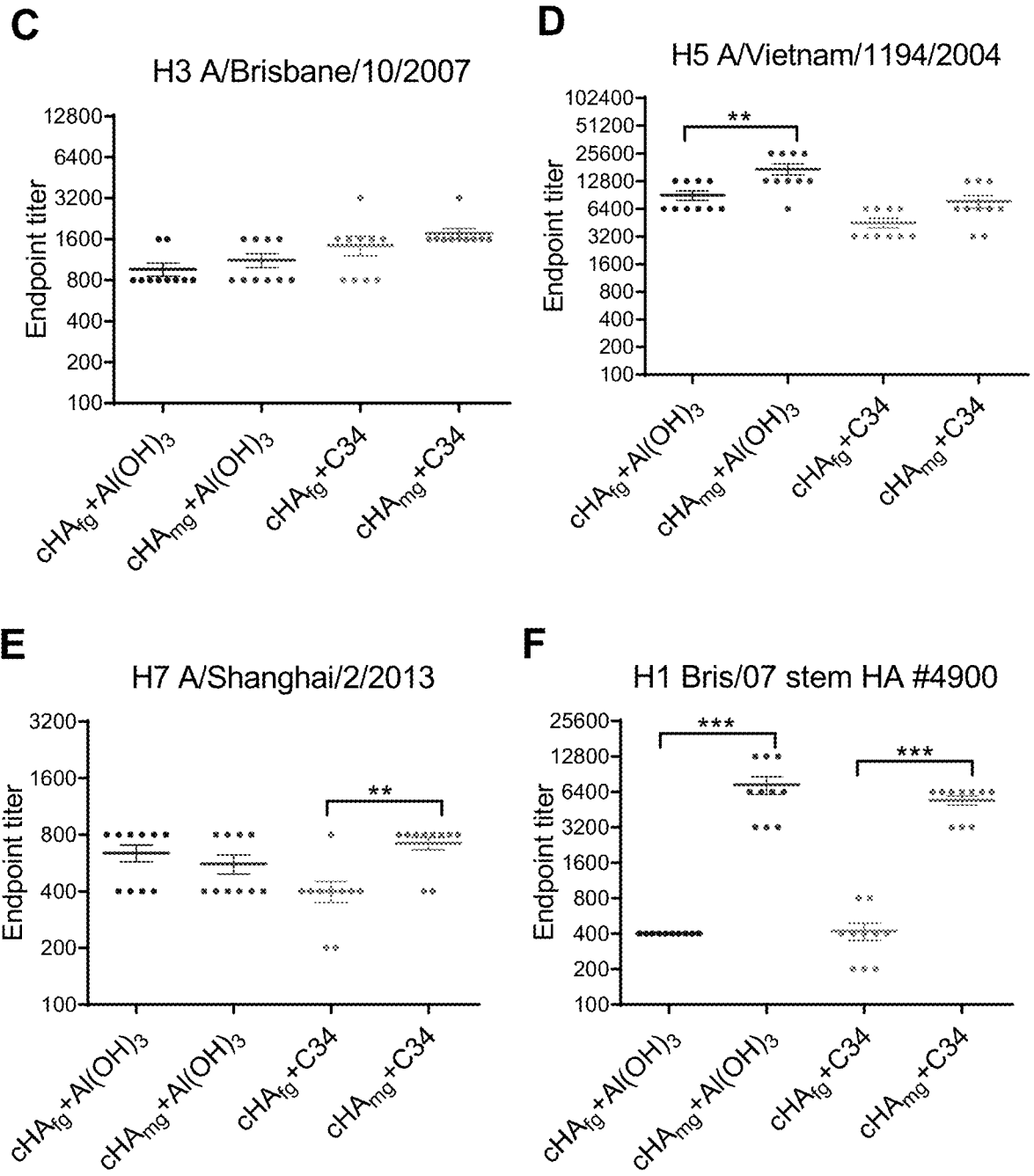

FIGS. 7 (A) to (F). HA binding activities of antisera from mice vaccinated with cHA$_{fg}$ and cHA$_{mg}$. BALB/c mice (n=10 per group) were immunized at two-week intervals with cHA$_{fg}$ or cHA$_{mg}$ adjuvanted with Al(OH)$_3$ or C34. The antibody titers from the mice vaccinated with Al(OH)$_3$-adjuvanted cHA$_{fg}$ and cHA$_{mg}$ vS. C34-adjuvanted cHA$_{fg}$ and cHA$_{mg}$ were measured on day 28 by ELISA with the A/California/07/2009 H1N1 HA protein (A), A/Brisbane/59/2007 H1N1 HA protein (B), A/Brisbane/10/2007 H3N2 HA protein (C), A/Vietnam/1194/2004 H5N1 HA protein (D), A/Shanghai/2/2013 H7N9 HA protein (E) and the A/Brisbane/59/2007 (Bris/07) stem HA (#4900) protein (F) as the coating antigen. The endpoint antibody titer was defined as the highest dilution of serum to produce an absorbance 2.5 times higher than the optical absorbance (OD) produced by the negative control (pre-immune serum). Data were examined by using two-way ANOVA from Prism; differences were considered statistically significant at P<0.01; *P<0.001. Data represents the mean±SEM.

Figure 8:
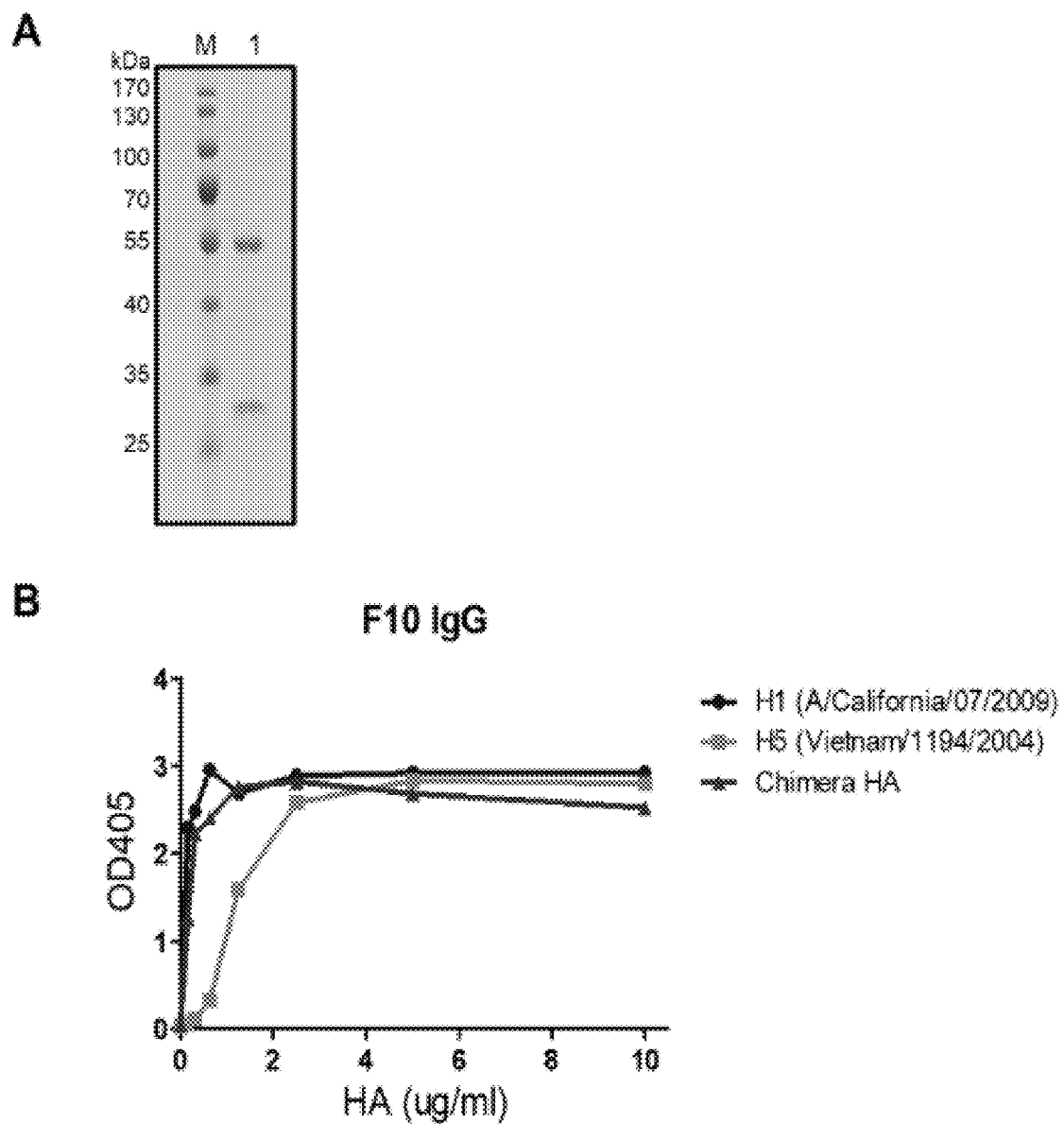

FIGS. 8 (A) and (B). Binding of stalk-reactive antibodies (F10 IgG) to recombinant H1, H5 and cHAs. (A) The purified F10 was analyzed by SDS/PAGE. M: molecular weight marker. Lane 1: F10 antibody. (B) The binding affinities of F10 IgG and various HA were measured by using ELISA. The x-axis shows the concentration of various HA proteins and the y-axis shows the absorbance value at OD405 nm.

Figure 9:
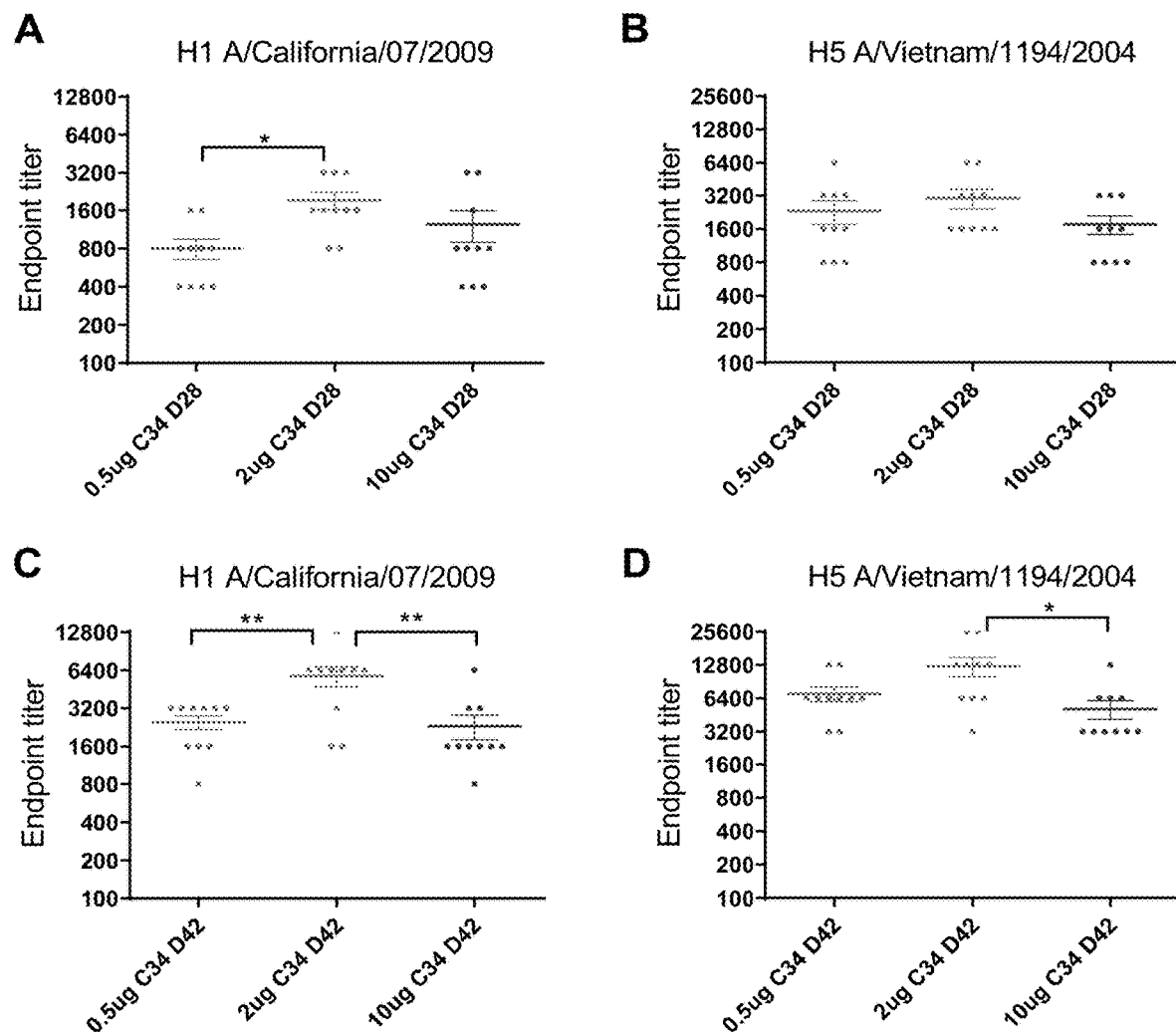

FIGS. 9 (A) to (D). Dose-dependent effects of C34 on antibody titers. BALB/c mice (n=10 per group) were injected at two-week intervals with 20 µg cHA adjuvanted with 0.5 µg, 2 µg or 10 µg of C34. Mice sera were collected two weeks after the second (D28) and third (D42) immunizations. The antibodies titers were measured by using ELISA with HA proteins of H1N1 A/California/07/2009 (A and C) and H5N1 Vietnam/1194/2004 (B and D). The P value of antibody titers was calculated by using two-way ANOVA from Prism; differences were considered statistically significant at *P<0.05; **P<0.01. Data represents the mean±SEM.

Figure 10:
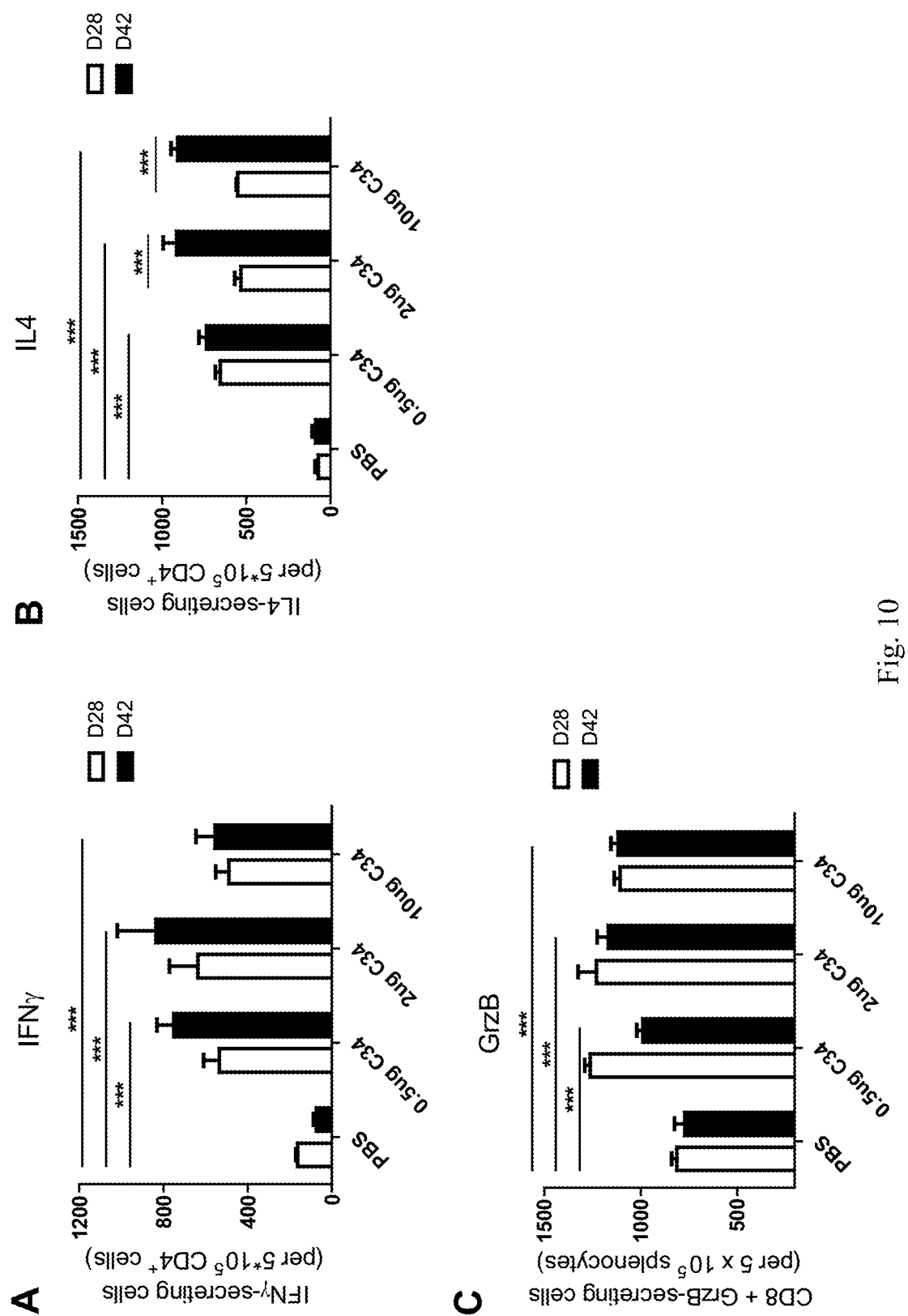

FIGS. 10 (A) to (C). Dose-dependent effects of C34 on antigen-specific cytokine-secreting cells. BALB/c mice (n=5 per group) were injected at two-week intervals with 20 µg of purified cHA adjuvanted with three different doses of C34 at 0.5, 2 and 10 µg. The splenocytes of cHA immunized mice were obtained after the second (D28) and third (D42) immunizations. (A) IFN-γ and (B) IL4-secreting cells were assessed by Elispot analysis. (C) The number of granzyme B producing $CD8^+$ T cell in splenocytes was determined by Elispot analysis using specific peptides. ***P<0.001. The P value were calculated with Prism software using two-way ANOVAs.

Figure 11:
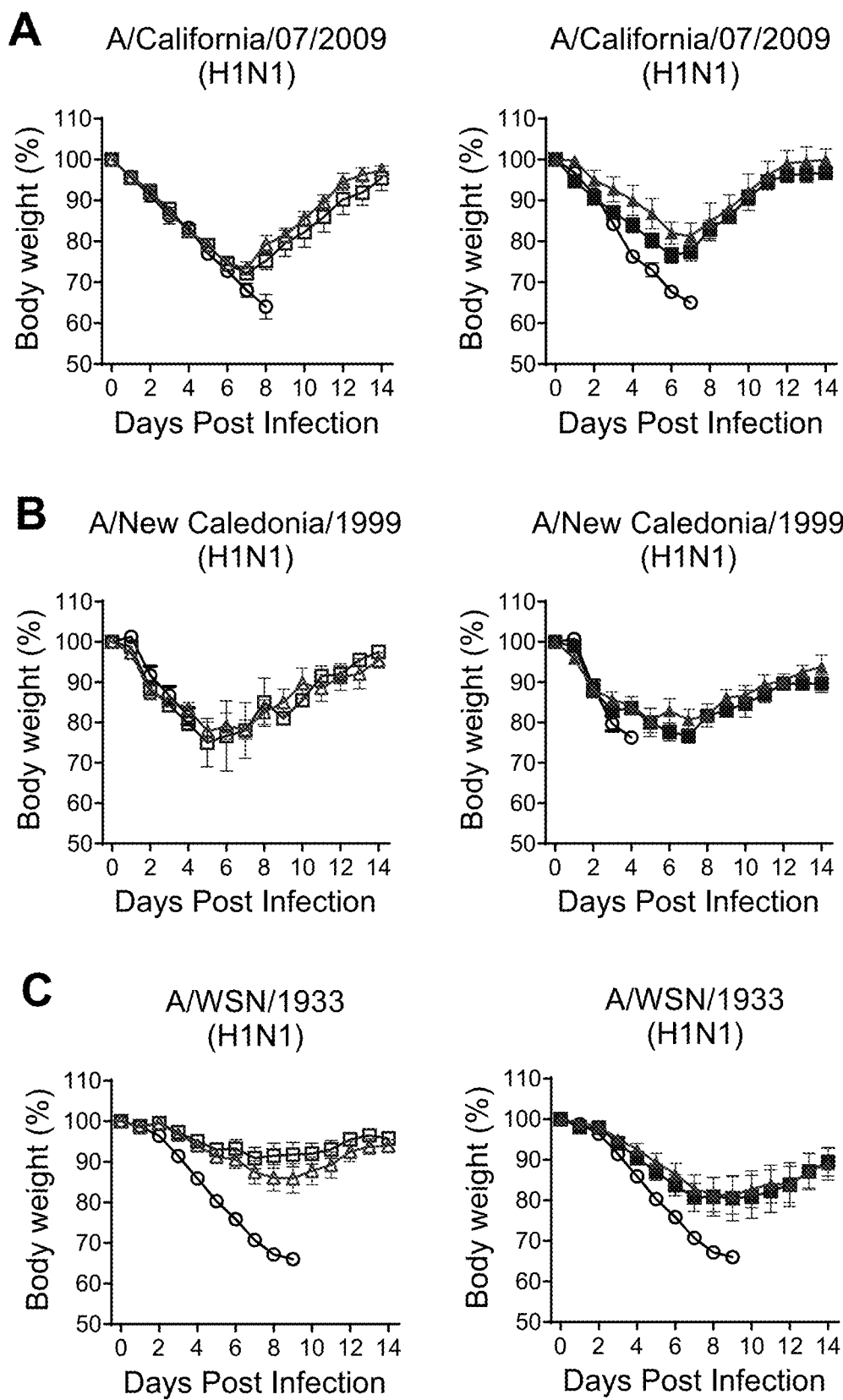
Figure 11:
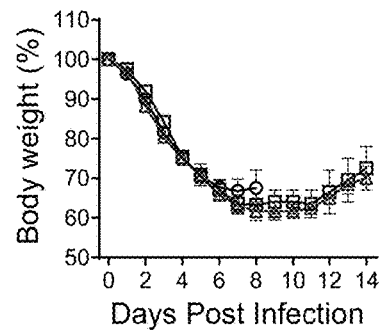
Figure 11:
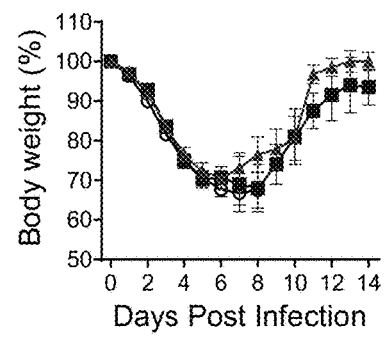
Figure 11:
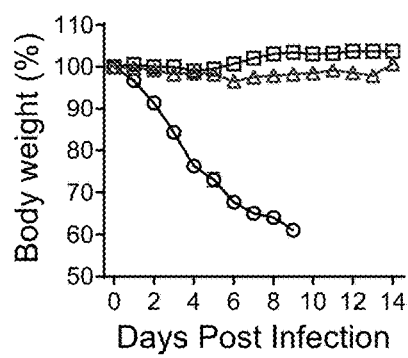
Figure 11:
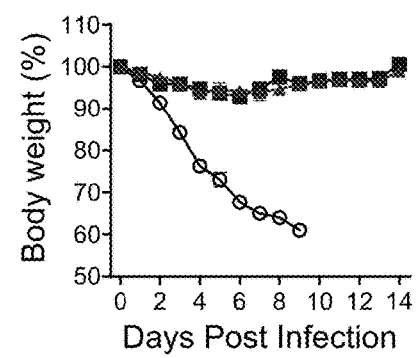
Figure 11:
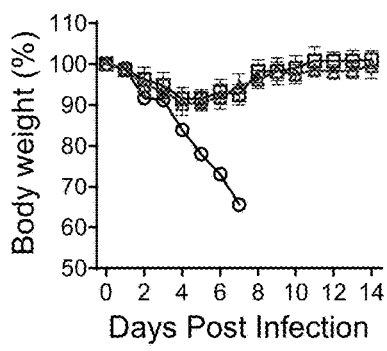
Figure 11:
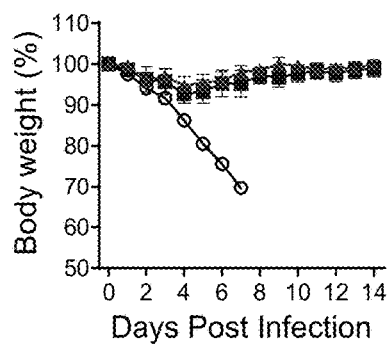

FIGS. 11 (A) to (F). The body weight of $cHA_{fg}$ or $cHA_{mg}$ vaccinated mice challenged by H1N1 and H5N1 viruses at lethal dose. Body-weight changes of immunized mice challenged with H1N1 A/California/07/2009 (A), H1N1 A/New Caledonia/1999 (B), H1N1 A/WSN/1933 (C), H1N1 A/Solomon Islands/03/2006 (D), H5N1 A/Vietnam/1194/2004 (E), or H5N1 A/Turkey/1/2005 (F) viruse were monitored for 14 days after infection. Body-weight change is presented as mean±SEM.

DETAILED DESCRIPTION OF THE INVENTION

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. By Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods in Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods in Cell and Molecular Biology (Mayer and Walker, eds., Academic Press, London, 1987); Antibodies: A Laboratory Manual, by Harlow and Lane s (Cold Spring Harbor Laboratory Press, 1988); and Handbook of Experimental Immunology, Volumes I-IV (D. M. Weir and C. C. Blackwell, eds., 1986).

Definitions

As used in the specification and claims, the singular forms "a", "an" and "the" include plural references unless the context clearly dictates otherwise. For example, the term "a chimeric transmembrane receptor" includes a plurality of chimeric transmembrane receptors.

As used herein, the terms "hemagglutinin" and "HA" refer to any hemagglutinin known to those with skill in the art. In certain embodiments, the hemagglutinin is influenza hemagglutinin, such as an influenza A hemagglutinin, an influenza B hemagglutinin, or an influenza C hemagglutinin. A typical hemagglutinin comprises domains known to those with skill in the art including a signal peptide, a stem domain, a globular head domain, a luminal domain, a transmembrane domain and a cytoplasmic domain.

As used herein, the terms "stem domain polypeptide," "HA stem domain," "influenza virus hemagglutinin stem domain polypeptide" and "HA stalk domain" refer to polypeptide comprising or consisting of one or more polypeptide chains that make up a stem domain of an influenza hemagglutinin. A stem domain polypeptide might be a single polypeptide chain, two polypeptide chains or more polypeptide chains.

As used herein, the terms "influenza virus hemagglutinin head domain polypeptide," "influenza virus hemagglutinin head domain," "HA globular head domain," and "HA head domain" refer to the globular head domain of an influenza hemagglutinin polypeptide.

As used herein, the term "antigen" is defined as any substance capable of eliciting an immune response.

As used herein, the term "immunogenicity" refers to the ability of an immunogen, antigen, or vaccine to stimulate an immune response.

As used herein, the term "epitope" is defined as the parts of an antigen molecule which contact the antigen binding site of an antibody or a T cell receptor.

As used herein, the term "vaccine" refers to a preparation that contains an antigen, consisting of whole disease-causing organisms (killed or weakened) or components of such organisms, such as proteins, glycoproteins, peptides, glycopeptides, glycolipids, polysaccharides, or any combination thereof that is used to confer immunity against the disease that the organisms cause. Vaccine preparations can be natural, synthetic or derived by recombinant DNA technology.

As used herein, the term "antigen specific" refers to a property of a cell population such that supply of a particular antigen, or a fragment of the antigen, results in specific cell proliferation.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

A consensus DNA sequence of avian influenza H5 (pCHA5-II) was used as a vaccine for administration in mice and the result was shown to have a broad protection against various H5 subtypes (Chen, M. W. et al. Broadly neutralizing DNA vaccine with specific mutation alters the antigenicity and sugar-binding activities of influenza hemagglutininin. *Proc. Natl Acad. Sci. USA* 108, 3510-3515 (2011)). The present disclosure reports the design and evaluation of various chimeric vaccines based on the most common avian influenza H5 and human influenza H1 sequences. Of these constructs, the chimeric HA (cHA) vaccine with consensus H5 as globular head and consensus H1 as stem was the best and shown to elicit strong CD4⁺ and CD8⁺ T-cell immune responses. Interestingly, the monoglycosylated cHA (cHA$_{mg}$) vaccine with only GlcNAc on each glycosite induced more stem-specific antibodies, with higher antibody-dependent cellular cytotoxicity (ADCC), better neutralizing and stronger cross-protection activities against H1, H3, H5 and H7 strains and subtypes. Moreover, the cHA$_{mg}$ vaccine combined with a glycolipid adjuvant designed for class switch further enhanced the vaccine efficacy with more IFN-γ, IL-4 and CD8+ memory T cells produced.

Chimeric Influenza Virus Hemagglutinin (HA) Polypeptide

The present disclosure provides a chimeric influenza virus hemagglutinin (HA) polypeptide used as immunogen or a vaccine to elicit CD4⁺ and CD8⁺ T-cell immune responses. Accordingly, the chimeric influenza virus HA polypeptide can prevent an influenza virus disease in a subject.

The chimeric influenza virus hemagglutinin (HA) polypeptide of the present disclosure comprises one or more stem domain sequence, each having at least 60% homology with a stem domain consensus sequence of H1 subtype HA (H1 HA) and/or H5 subtype HA (H5 HA) fused with one or more globular head domain sequence, each having at least 60% homology with a globular head consensus sequence of H1 subtype HA (H1 HA) or H5 subtype HA (H5 HA).

As used herein, the term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity and identity are quantitative terms that define the degree of sequence match between two compared sequences. In some embodiments, polymeric molecules are considered to be "homologous" to one another if their sequences are at least 60%, 65%, 70%, 75%, 80%, 85%, 90%, 95%, or 99% identical or similar.

In some embodiments the polypeptide according to the present disclosure may comprise one or more sequences having at least 60% homology with a consensus sequence of H1 HA or H5 HA over known human and avian influenza virus strains. In some embodiments, the homology is at least 65%, 70%, 75%, 80%, 85%, 90%, 95%, 96%, 97%, 98%, 99% or 100%. In some embodiments, the stem domain sequence is an N-terminal stem segment of H1 HA or a C-terminal stem segment of H1 HA; an N-terminal stem segment of H1 HA or a C-terminal stem segment of H1+H5 HA sequences; or an N-terminal stem segment of H5 HA or a C-terminal stem segment of H1+H5 HA sequences.

In some embodiments, the stem domain consensus sequence of H1 HA and/or H5 HA comprises an amino acid sequence of SEQ ID NO: 1, SEQ ID NO: 2, SEQ ID NO: 5, SEQ ID NO: 6, SEQ ID NO: 9, or SEQ ID NO: 10.

(H1 STEM)
SEQ ID NO: 1
DTLCIGYHANNSTDTVDTVLEKNVTVTHSVNLLEDKHNGKL (H1 STEM)
SEQ ID NO: 2
NTTCQTPKGAINTSLPFQNIHPITIGKCPKYVKSTKLRLATGLRNVPSI

QSRGLFGAIAGFIEGGWTGMVDGWYGYHHQNEQGSGYAADLKSTQNAID

KITNKVNSVIEKMNTQFTAVGKEFNHLEKRIENLNKKVDDGFLDIWTYN

AELLVLLENERTLDYHDSNVKNLYEKVRNQLKNNAKEIGNGCFEFYHKC

DNTCMESVKNGTYDYPKYSEEAKLNREEIDGVKLESTRIYQ (H1 STEM)
SEQ ID NO: 5
DTLCIGYHANNSTDTVDTVLEKNVTVTHSVNLLEDKHNGKL (H1+H5 STEM)
SEQ ID NO: 6
NTTCQTPKGAINTSLPFQNIHPITIGKCPKYVKSTKLRLATGLRNVPSI

QSRGLFGAIAGFIEGGWQGMVDGWYGYHHSNEQGSGYAADKESTQKAID

GVTNKVNSIIDKMNTQFEAVGREFNNLERRIENLNKKMEDGFLDVWTYN

AELLVLMENERTLDFHDSNVKNLYDKVRLQLRDNAKELGNGCFEFYHKC

DNECMESVRNGTYDYPQYSEEARLKREEISGV (H5 STEM)
SEQ ID NO: 9
DQICIGYHANNSTEQVDTIMEKNVTVTHAQDILEKTHNGKL (H5+H1 STEM)
SEQ ID NO: 10
NTKCQTPMGAINSSMPFHNIHPLTIGECPKYVKSNRLVLATGLRNSPQR

ERRRKKRGLFGAIAGFIEGGWTGMVDGWYGYHHQNEQGSGYAADLKSTQ

NAIDKITNKVNSVIEKMNTQFTAVGKEFNHLEKRIENLNKKVDDGFLDI

WTYNAELLVLLENERTLDYHDSNVKNLYEKVRNQLKNNAKEIGNGCFEF

YHKCDNTCMESVKNGTYDYPKYSEEAKLNREEIDGV

In one embodiment, the globular head domain consensus sequence of H1 HA or H5 HA comprises an amino acid sequence of SEQ ID NO:3, SEQ ID NO: 7 or SEQ ID NO:11.

(H5 GLOBULAR HEAD)
SEQ ID NO: 3
CDLDGVKPLILRDCSVAGWLLGNPMCDEFINVPEWSYIVEKANPANDLC

YPGNENDYEELKHLLSRINHFEKIQIIPKSSWSDHEASSGVSSACPYQG

KSSFFRNVVWLIKKNSTYPTIKRSYNNTNQEDLLVLWGIHHPNDAAEQT

RLYQNPTTYISVGTSTLNQRLVPKIATRSKVNGQSGRMEFFWTILKPND

AINFESNGNFIAPEYAYKIVKKGDSTIMKSELEYGNC (H1 GLOBULAR HEAD)
SEQ ID NO: 7
CKLRGVAPLHLGKCNIAGWILGNPECESLSTASSWSYIVETSSSDNGTC

YPGDFIDYEELREQLSSVSSFERFEIFPKTSSWPNHDSNKGVTAACPHA

GAKSFYKNLIWLVKKGNSYPKLSKSYINDKGKEVLVLWGIHHPSTTADQ

QSLYQNADAYVFVGTSRYSKKFKPEIAIRPKVRDQEGRMNYYWTLVEPG

DKITFEATGNLVVPRYAFAMERNAGSGIIISDTPVHDC (H5 GLOBULAR HEAD)
SEQ ID NO: 11
CDLDGVKPLILRDCSVAGWLLGNPMCDEFINVPEWSYIVEKANPANDLC

YPGNENDYEELKHLLSRINHFEKIQIIPKSSWSDHEASSGVSSACPYQG

KSSFFRNVVWLIKKNSTYPTIKRSYNNTNQEDLLVLWGIHHPNDAAEQT

RLYQNPTTYISVGTSTLNQRLVPKIATRSKVNGQSGRMEFFWTILKPND

AINFESNGNFIAPEYAYKIVKKGDSTIMKSELEYGNC

In one embodiment, the chimeric influenza virus HA polypeptide comprises an amino acid sequence of SEQ ID NO: 4, SEQ ID NO: 8, or SEQ ID NO: 12.

(Chimeric H5/1)
SEQ ID NO: 4
DTLCIGYHANNSTDTVDTVLEKNVTVTHSVNLLEDKHNGKLCDLDGVKP

LILRDCSVAGWLLGNPMCDEFINVPEWSYIVEKANPANDLCYPGNFNDY

EELKHLLSRINHFEKIQIIPKSSWSDHEASSGVSSACPYQGKSSFFRNV

VWLIKKNSTYPTIKRSYNNTNQEDLLVLWGIHHPNDAAEQTRLYQNPTT

YISVGTSTLNQRLVPKIATRSKVNGQSGRMEFFWTILKPNDAINFESNG

NFIAPEYAYKIVKKGDSTIMKSELEYGNCNTTCQTPKGAINTSLPFQNI

HPITIGKCPKYVKSTKLRLATGLRNVPSIQSRGLFGAIAGFIEGGWTGM

VDGWYGYHHQNEQGSGYAADLKSTQNAIDKITNKVNSVIEKMNTQFTAV

GKEFNHLEKRIENLNKKVDDGFLDIWTYNAELLVLLENERTLDYHDSNV

KNLYEKVRNQLKNNAKEIGNGCFEFYHKCDNTCMESVKNGTYDYPKYSE

EAKLNREEIDGVKLESTRIYQ (Swap H1/5)
SEQ ID NO: 8
DTLCIGYHANNSTDTVDTVLEKNVTVTHSVNLLEDKHNGKLCKLRGVAP

LHLGKCNIAGWILGNPECESLSTASSWSYIVETSSSDNGTCYPGDFIDY

EELREQLSSVSSFERFEIFPKTSSWPNHDSNKGVTAACPHAGAKSFYKN

LIWLVKKGNSYPKLSKSYINDKGKEVLVLWGIHHPSTTADQQSLYQNAD

AYVFVGTSRYSKKFKPEIAIRPKVRDQEGRMNYYWTLVEPGDKITFEAT

GNLVVPRYAFAMERNAGSGIIISDTPVHDCNTTCQTPKGAINTSLPFQN

IHPITIGKCPKYVKSTKLRLATGLRNVPSIQSRGLFGAIAGFIEGGWQG

MVDGWYGYHHSNEQGSGYAADKESTQKAIDGVTNKVNSIIDKMNTQFEA

VGREFNNLERRIENLNKKMEDGELDVWTYNAELLVLMENERTLDFHDSN

VKNLYDKVRLQLRDNAKELGNGCFEFYHKCDNECMESVRNGTYDPQYS

EEARLKREEISGV (Swap H5/1)
SEQ ID NO: 12
DQICIGYHANNSTEQVDTIMEKNVTVTHAQDILEKTHNGKLCDLDGVKP

LILRDCSVAGWLLGNPMCDEFINVPEWSYIVEKANPANDLCYPGNFNDY

EELKHLLSRINHFEKIQIIPKSSWSDHEASSGVSSACPYQGKSSFFRNV

VWLIKKNSTYPTIKRSYNNTNQEDLLVLWGIHHPNDAAEQTRLYQNPTT

YISVGTSTLNQRLVPKIATRSKVNGQSGRMEFFWTILKPNDAINFESNG

NFIAPEYAYKIVKKGDSTIMKSELEYGNCNTKCQTPMGAINSSMPFHNI

HPLTIGECPKYVKSNRLVLATGLRNSPQRERRRKKRGLFGAIAGFIEGG

WTGMVDGWYGYHHQNEQGSGYAADLKSTQNAIDKITNKVNSVIEKMNTQ

FTAVGKEFNHLEKRIENLNKKVDDGFLDIWTYNAELLVLLENERTLDYH

DSNVKNLYEKVRNQLKNNAKEIGNGCFEFYHKCDNTCMESVKNGTYDYP

KYSEEAKLNREEIDGV

In some embodiments, to enhance the immunogenicity, one or more glycosites on HA are monoglycosylated. Preferably, the monoglycosylated HA has only N-Acetylglucosamine (GlcNAc) on each glycosite.

The chimeric influenza virus HA polypeptide may be produced by any suitable method, many of which are known to those skilled in the art. For example, the proteins may be chemically synthesized, or produced using recombinant DNA technology (e.g. in bacterial cells, in cell culture (mammalian, yeast or insect cells), in plants or plant cells, or by cell-free prokaryotic or eukaryotic-based expression systems, by other in vitro systems, etc.) Accordingly, the present disclosure provides a recombinant polynucleotide comprising a nucleic acid sequence encoding a polypeptide of the present disclosure and optionally a nucleic acid sequence encoding a signal peptide. The present disclosure provides a vector comprising a recombinant polynucleotide of the present disclosure. The embodiments of the polypeptide of the present disclosure are described herein. In one embodiment, the signal peptide comprises a sequence of SEQ ID NO: 13 (MEKIVLLLAIVSLVKS) or SEQ ID NO: 14 (MKAILVVLLYTFATANA). A host cell comprising a vector of the present disclosure is also provided.

Immunogenic Compositions

The immunogenic composition preferably comprises at least one pharmaceutically acceptable carrier and/or adjuvant. In one embodiment, the adjuvant is a glycolipid adjuvant. Examples of the adjuvant include, but are not limited to, Al(OH)$_3$, AlPO$_4$, C34, squalene and QS21.

A chimeric influenza virus HA polypeptide of the present disclosure may be formulated or administered in combination with one or more pharmaceutically-acceptable excipients. Immunogenic/vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

The immunogenic composition is administered in a manner compatible with the dosage formulation, and in an amount that is therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art. Suitable regimes for initial administration and booster doses are also variable but may include an initial administration followed by subsequent administrations. The dosage of the vaccine may also depend on the route of administration and varies according to the size of the host.

Formulations of the vaccine compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single-or multi-dose unit.

Applications

It has been known for some time that cytotoxic T lymphocytes (CTL) may provide an immune response against influenza virus strains. Recent studies have shown that a CTL response in humans may be directed towards multiple epitopes.

Provided herein are methods for prevention of an influenza virus disease in humans and other mammals. Also provided is a method of eliciting an immune response in a subject against influenza virus. The method involves administering an effective amount of a chimeric influenza virus HA polypeptide or an immunogenic composition/vaccine of the present disclosure to the subject, thereby inducing in the subject an immune response specific to influenza virus strains (such as H1, H3, H5 and H7 strains and subtypes). Preferably, the methods elicit $CD4^+$ and $CD8^+$ T-cell immune responses. More preferably, the methods induce stem-specific antibodies, with higher antibody-dependent cellular cytotoxicity (ADCC), better neutralizing and stronger cross-protection activities against H1, H3, H5 and H7 strains and subtypes. The methods also enhance the vaccine efficacy with more IFN-γ, IL-4 and CD8+ memory T cells produced.

The antibody titer in the subject is increased following vaccination. In exemplary aspects, the immune compositions or vaccines of the present disclosure are used to provide prophylactic protection from influenza. Prophylactic protection from influenza can be achieved following administration of a vaccine or combination vaccine, of the present disclosure. Vaccines (including combination vaccines) can be administered once, twice, three times, four times or more but it is likely sufficient to administer the vaccine once (optionally followed by a single booster). Dosing may need to be adjusted accordingly.

A prophylactically effective dose is a therapeutically effective dose that protects against the influenza virus at a clinically acceptable level. In some embodiments the therapeutically effective dose is a dose listed in a package insert for the vaccine.

The chimeric influenza virus HA polypeptide or an immunogenic composition/vaccine of the present disclosure may be administered by any route which results in a therapeutically effective outcome. These include, but are not limited to, intradermal, intramuscular, and/or subcutaneous administration. In some embodiments, a chimeric influenza virus HA polypeptide or an immunogenic composition/vaccine of the present disclosure may be administered intramuscularly or intradermally, similarly to the administration of inactivated vaccines known in the art.

This invention is not limited in its application to the details of construction and the arrangement of components set forth in the following description or illustrated in the drawings. The invention is capable of other embodiments and of being practiced or of being carried out in various ways.

EXAMPLES

Methods

Vaccine and plasmid construction. All 102 full-length HA sequences from H1N1 viruses available in early 2009~2013 were downloaded from the NCBI database and aligned by the ClustalW algorithm from the BioEdit program. The most conserved amino acid at each position was chosen to create a consensus H1 sequence. The consensus hemagglutinin H5 (pCHA5-II) sequence was generated as described previously. The nucleotide sequences of consensus hemagglutinin H5 (pCHA5-II) and consensus H1 were cloned into the pcDNA expression vector, and the resulting plasmids were used as the templates for swap and chimeric HA construction. Swap H1/5 is composed of H1 as HA1 (amino acid 1~327 of SEQ ID NO: 8) and H5 as HA2 (amino acid 328~503 of SEQ ID NO: 8), giving H1 as globular head and H1+H5 (HA2) stem. Swap H5/1 is composed of H5 as HA1 (amino acid 1~330 of SEQ ID NO: 12) and H1 as HA2 (amino acid 331~506 of SEQ ID NO: 12), giving H5 as globular head and H5+H1 (HA2) stem. For chimeric H5/1 construct, the globular head domain is composed of the amino acid sequence between residues C42 and C274 of SEQ ID NO: 4 (H3 numbering) and the stem region is comprised of portions of HA1 and HA2 subunits (amino acids 1~41 of SEQ ID NO: 4 and 275~511 of SEQ ID NO: 4). The transmembrane domain was replaced with the additional residues from the bacteriophage T4 fibritin foldon trimerization sequence, thrombin cleavage site and $(His)_6$-tag at the C-terminus of the HA. Both DNA sequences of consensus HA were optimized for expression by using human-preferred codons and various regions were amplified by PCR and subsequently cloned into the pcDNA vector for expression. Furthermore, the HA gene from influenza virus seasonal H1N1 Brisbane/59/2007, pandemic H1N1 California/07/2009, H3N2 Brisbane/10/2007, H7N9 A/Shanghai/2/2013 and avian flu H5N1 Vietnam/1194/2004 were also optimized, synthesized, and cloned into the pcDNA expression vector. The sequences were confirmed by DNA sequencing and prepared in high quality for protein expression and purification.

Expression of recombinant secreted HA from expressed cells. Human epithelial kidney (HEK) 293T and HEK293S cells were routinely maintained in DMEM (Gibco) supplemented with 10% fetal bovine serum (Gibco). For transient transfection, 293T or 293S cells were seeded in a 10 cm dish (Nunc, Roskilde, Denmark) and all the procedures were performed according to the manufacture's protocol. Briefly, 293T or 293S cells at 80% confluency were transfected with Mirus TransIT®-LT1 (Mirus Bio) transfection reagent using a 3:1 ratio of reagent to plasmid DNA. TransIT®-LT1 reagents were diluted with Opti-MEM (Gibco) and the mixture was incubated for 5-20 minutes at room temperature. The solution was added with plasmid DNA and mixed completely followed by incubation for 15-30 minutes. Prior to transfection, cells were replaced with fresh DMEM (Gibco) medium supplemented with 10% fetal bovine serum. The TransIT®-LT1 reagent/DNA complex was added to the cells and incubated for 48 h at 37° C. The expression of hemagglutinin was confirmed with immunoblots using anti-$(his)_6$ antibodies (Qiagen) or specific anti-hemagglutinin antibodies and the horseradish peroxidase (HRP)-conjugated secondary antibodies (PerkinElmer).

Purification of recombinant secreted hemagglutinins. For expression in human 293T cells, pcDNA carrying the gene of interest was prepared in high quality and transfected to the cells with Mirus TransIT®-LT1 (Mirus Bio). After 48 h of transfection, the medium was collected and the cells were clarified by centrifugation at 1,000×g for 10 mins. The supernatant was purified by Ni-NTA (nickel-nitrilotriacetic acid) affinity column (GE Healthcare). The supernatants were loaded onto Ni-NTA affinity column pre-equilibrated in 20 mM Tris-HCl pH 8.0 and 300 mM NaCl. The unbound proteins were washed out with imidazole gradient from 25 to 50 mM in 20 mM Tris-HCl pH 8.0 and 300 mM NaCl (Buffer A). Then, the HA protein was eluted with 100 to 300 mM imidazole gradient in Buffer A. The purified HA proteins were concentrated by Amicon Ultrafiltration Unit (MW30K cutoff) (Millipore) in PBS, pH 7.4. The purity was monitored by using SDS-PAGE and the proteins were confirmed using Western blot with anti-(his)$_6$ antibodies (Qiagen) or specific anti-hemagglutinin antibodies and the horseradish peroxidase-conjugated secondary antibodies (PerkinElmer). Finally, the trimer form of HA proteins was obtained by using size-exclusion column, Superdex 200 Increase 10/300 GL gel filtration column (GE Healthcare).

Preparation of mono-glycosylated HA proteins. HEK293S cells, which are deficient in N-acetylglucosaminyltransferase I, were used to produce HA with high-mannose glycans[31]. The purified HA protein from HEK293S cells was treated with Endo H (NEB) at 20° C. for overnight to produce the monoglycosylated $HA_{mg}$. The ratio of proteins to Endo H was 3 to 1 (w/v) for HA. Endo H and mono-glycosylated HA protein were then separated by Superdex 200 Increase 10/300 GL gel filtration column (GE Healthcare). The $HA_{mg}$ proteins were concentrated by Amicon Ultrafiltration Unit (MW30K cutoff) (Millipore) in PBS, pH 7.4 and confirmed by SDS-PAGE and LC-MS/MS analysis.

Identification of N-linked glycosylation on HA proteins. Ten micrograms of protein were run on SDS-PAGE and were prepared for in-gel digestion. The desired proteins bands were excised with a sharp scalpel, diced into 1 mm pieces and placed into 1.3 ml eppendorf tubes. After washing twice with 500 µl of 25 mM ammonium bicarbonate in 50% ACN (acetonitrile) for 3 min, the gel pieces were dried using a SpeedVac evaporator (Thermo). The dried samples were reduced by the addition of 100 µl of 50 mM dithiothreitol (DTT) in 25 mM ammonium bicarbonate (pH 8.5) at 37° C. for 1 h followed by centrifuge at 10,000 g for 1 min. The solution was removed and the gel samples were proceeded to an alkylation step by the addition of 100 µl of 100 mM iodoacetamide (IAA) in 25 mM ammonium bicarbonate (pH 8.5) and incubated in the dark at room temperature for 1 h. After washing with 500 µl of 50% acetonitrile in 25 mM ammonium bicarbonate (pH 8.5) and 500 µl of 100% acetonitrile, the samples were centrifuged at 10,000 g for 1 min and the supernatant was removed completely. The gel samples were dried at a SpeedVac evaporator and redissolved with 200 µl of 25 mM ammonium bicarbonate (pH 8.5). Gel samples were then treated with 0.5 µg trypsin (Promega, Madison, WI, USA) and 1 µg chymotrypsin (Promega, Madison, WI, USA) for overnight. After an overnight digestion, the samples were added with 100 µl of 50% acetonitrile in 5% TFA. The samples were sonicated for 10 sec, and then stopped for 10 sec. The processes were repeated 10 times. The supernatant containing peptide mixtures was removed from the sample tubes and transferred to new tubes. The procedure was repeated twice. The combined supernatants were dried in SpeedVac concentrator and processed for LC-MS/MS analysis.

Endotoxin measurement. Endotoxin levels were determined using the Pierce® LAL Chromogenic Endotoxin Quantitation Kit (Thermo Scientific). Protein samples were diluted in 10, 20, 100, and 1000-fold, while endotoxin standards were prepared as 10, 5, 2.5, 1.25, 0.63, 0.31, 0.15, and 0 ng/ml. After the microplate was equilibrated in a heating block for 10 mins at 37° C., protein samples or standards were mixed with Limulus Amebocye Lasate (LAL) Pyrochrome reagent (final volume 100 µl) (1:1) in endotoxin-free wells at 37° C. for 10 minutes. One hundred µls of substrate solution were added to each well and the plates were incubated at 37° C. for 6 mins. The reaction was stopped with the addition of 50 µl stop reagent (25% acetic acid). The absorbance of wells was measured at 405 nm using a SpectraMax M5 (Molecular Devices, Sunnyvale, CA, USA). A standard curve was obtained by plotting the absorbance versus the corresponding concentrations of the standards. The standard curve was used to determine the endotoxin concentration of the samples. Endotoxin values of all purified proteins were <0.5 ng/ml.

Mice vaccination. Adjuvant C34 was chemically synthesized as described and dissolved in DMSO. Female 6- to 8-week-old BALB/c mice (n=10 per group) were immunized intramuscularly with 20 µg of purified chimeric $HA_{fg}$ or $HA_{mg}$ proteins in PBS, pH 7.4, and mixed with 50 µg of aluminum hydroxide (Alum; Sigma) or 2 µg of C34. Control mice were injected with phosphate buffer saline (PBS). Three vaccinations were given at two-week intervals. Blood was collected 14 days after the second or third immunization. The blood was incubated at 37° C. for 30 minutes, and centrifuged at 1,2000 rpm for 10 mins to collect serum. The HA-specific antibodies in serum collected from vaccinated mice were assessed by enzyme-linked immunosorbent assay (ELISA) and neutralization assay.

Determination of HA-specific antibodies by ELISA. HA-specific antibody titers were detected by ELISA using H1N1 A/Brisbane/59/2007, H1N1 A/California/07/2009, H3N2 Brisbane/10/2007, H7N9 A/Shanghai/2/2013 and H5N1 Vietnam/1194/2004 HA proteins as the substrates. Ninety-six-well ELISA plate (Greiner bio-one, Frickenhausen, Germany) was coated with 100 µl of protein diluted in ELISA coating buffer, 100 mM sodium bicarbonate (pH 8.8), at a concentration of 5 µg/ml per well, and covered with a plastic sealer at 4° C. for overnight. After the plates were blocked with 1% BSA in TBST (137 mM NaCl, 20 mM Tris-base, 0.05% Tween 20, pH 7.4) at 37° C. for 1 h and washed 3 times with TBST, the plates were incubated with 200 µl of mouse serum in 2-fold serial dilutions at 37° C. for 2 h. After serum was moved and the plate was washed 6 times, HA-specific IgG was monitored by using 200 µl of secondary HRP-labeled anti-mouse antibody (1:8000) (PerkinElmer, Waltham, MA, USA). After 1 h of incubation at 37° C., the plates were washed 6 times with TBST and developed with 100 µl of the Super Aquablue ELISA substrate (eBioscience, San Diego, CA, USA) for 1 min. The reaction was stopped with the addition of 100 µl of 0.625 M oxalic acid. The absorbance of wells was measured at 405 nm using a SpectraMax M5 (Molecular Devices, Sunnyvale, CA, USA). The endpoint antibody titer was defined as the highest dilution of serum to produce an absorbance 2.5 times higher than the optical absorbance (OD) produced by the negative control (pre-immune serum). The background endpoint antibody titer was assigned as less than 1:50.

Harvest of bone marrow-derived dendritic cells. The GM-CSF-cultured bone marrow-derived dendritic cells (BMDCs) were prepared as described previously. Briefly, bone marrow single cell suspensions were subjected to RBC lysis to remove the red blood cells (RBCs). The remaining cells were cultured in 10 ml of RPMI 1640 supplemented with 20 ng/ml murine GM-CSF (eBioscience), 10% FBS (BenchMark), 50 µM 2-ME, 100 units/mL penicillin, and 100 µg/mL streptomycin. Cells were plated into each petri dish to achieve the final cell density of $2 \times 10^6$ cells/petridish. The culture was replenished by adding 10 ml of fresh culture medium containing 20 ng/ml murine GM-CSF at day 3 and refreshed with one-half the volume of complete culture medium as described above at day 6. At day 8, immature BMDCs were harvested by collecting nonadherent cells by gently pipetting and re-plated the cells at a density of $10^6$/ml. For CD8+ T cell assay, immature BMDCs were co-cultured with CD8+ T cell and chimeric HA proteins (0.1 mg/well in 100 μL) for 48 h. The number of granzyme B producing CD8+ T cells was determined by flow cytometric analysis after washing.

Enzyme-linked immunospot (ELISpot) assay. ELISPOT plates were coated with anti-mouse IFN-γ, IL-4 (Mabtech AB, Stockholm, Sweden) or granzyme B (R&D Systems) according to the manufacturer's instructions. The plates were washed four times and incubated for 30 min with RPMI-1640 supplemented with 10% Fetal bovine serum (Gibco). For the detection of IFN-γ, IL-4 and granzyme B-secreting cells from chimera-immunized mice, splenocytes were collected and cultured at $5 \times 10^5$ per well at 37° C. in 5% $CO_2$ for 24 h with specific peptides from HA for restimulation. The cells were removed and incubated with biotinylated anti-mouse IFN-γ, IL-4 (Mabtech AB) or granzyme B (R&D Systems) specific antibody. The plates were washed five times before the addition of streptavidin-ALP conjugate and developed with ready-to-use BCIP/NPT substrate. Following drying, the number of resulting spots was analyzed with an Immune Spot Reader (Cellular Technology Ltd.). Data were obtained from triplicate wells.

Neutralization assay. The culture supernatant containing 100 $TCID_{50}$ of virus was mixed with equal volume of two-fold serially diluted serum and incubated at 37° C. for 1 h. The mixtures were then added to MDCK cells in each well of a 96-well plate and incubated at 37° C. for 3 days. The cells were added 30 μl of CellTiter-Glo (Promega) to determine the number of viable cells based on quantitation of the ATP present. The neutralizing activity of serum was determined as the maximal dilution fold that significantly protected cells from virus-induced death.

Microneutralization assay. An infection medium (DMEM supplemented with 0.3% BSA, 2 μg/ml TPCK-Trypsin) containing virus at 100 $TCID_{50}$ was mixed in equal volume with two-fold serial dilutions of serum and incubated at 37° C. for 1 h. The mixture was then added to MDCK cells ($1.5 \times 10^4$ cells per well) in each well of a 96-well plate and incubate at 37° C. for 16-20 h. The cells were washed with PBS, fixed in acetone/methanol solution (vol/vol 1:1), and blocked with 5% skim milk. After 1 h of incubation at 37° C., the wells were washed 6 times with PBST, and the virus titer was monitored by using 100 μl of mAb against influenza A NP (1:2500). After 1 h of incubation at 37° C., the wells were washed 6 times with PBST and added 100 μl of secondary HRP-labeled anti-rabbit antibody (1:5000) (PerkinElmer, Waltham, MA, USA). After 1 h of incubation at 37° C., the wells were washed 6 times with PBST again and developed with 50 μl of the 1-Step Ultra TMB substrate (Thermo) for 1 min. The reaction was stopped with the addition of 50 μl of 1 M $H_2SO_4$. The absorbance of wells was measured at 450 nm using a SpectraMax M5 (Molecular Devices, Sunnyvale, CA, USA).

Antibody dependent cell mediated cytotoxicity reporter assay. MDCK cells ($1 \times 10^4$ cells per well) in each well of a 96-well flat-bottom plate were incubated at 37° C. for 24 h. The next day, $1 \times 10^4$ MDCK cells were infected with influenza viruses at multiplicity of infection (MOI) of 1 for 24 h. The medium was then replaced with Roswell Park Memorial Institute (RPMI) medium 1640 supplemented with 4% Low IgG Serum followed by addition of serial dilutions of antisera from chimeric HA protein-vaccinated mice and incubated at 37° C. for 30 min. Jurkat effector cells expressing mouse FcγRIII (Promega) were suspended in RPMI 1640 medium containing 4% low IgG FBS and the target cells: effector cells ratio of 1:5 were added to the infected MDCK cells. After incubation at 37° C. for 6 h, assay plates were removed from the 37° C. incubator and equilibrated for 15 min at ambient temperature before Bio-Glo™ Luciferase Assay Buffer (Promega) was added in a 1:1 ratio. Luminescence was measured on a CLARIOstar plate-reader.

Virus challenge experiments. Two weeks after three vaccinations at two week intervals, the immunized mice were challenged intranasally with 10 $LD_{50}$ (the virus doses leading to 50% of the death of mice) of H1N1 California/07/2009, H1N1 A/New Caledonia/1999, H1N1 A/WSN/1933, H1N1 A/Solomon Islands/03/2006 and a reassortant H5N1 virus A/Vietnam/1194/2004/NIBRG14 and H5N1 A/Turkey/1/2005/NIBRG23 . . . . After infection, the mice were observed daily for 14 days, and survival and body weight were recorded. The percentage of body weight was calculated for each individual animal per group by comparing the daily weight to the pre-challenge weight, and mice losing more than 25% of their initial weight were sacrificed and scored as dead. Mouse studies were approved by the Institutional Animal Care and Use Committee of Academia Sinica. All animal experiments were performed under biosafety level-3 enhancement conditions.

Expression and purification of recombinant F10 antibodies. The plasmid that encodes the F10 antibody was transfected into serum-free adapted FreeStyle™ 293F cells by using polyethyleneimine and was cultured in FreeStyle™ 293 Expression Medium (Gibco) in 125 ml sterile Erlenmeyer flasks, rotating at 135 rpm on an orbital shaker platform. The supernatant was collected 72 h after transfection and the cells were clarified by centrifugation at 1,000×g for 10 mins. The supernatants were loaded onto Protein-A column (GE Healthcare) that was pre-equilibrated in 5 Column Volumes (CV) of phosphate buffered saline (PBS) washing buffer (pH 7.0), followed by 5 CV of washing buffer. The F10 antibody was eluted with 0.2 M glycine buffer (pH 2.5) and the fractions were collected into tubes containing 0.5 mL 1 M Tris-HCl pH 9.0 for neutralization. The purity was monitored by using SDS-PAGE.

Statistical analysis. The animal experiments used for evaluation of immune responses were repeated at least three times (n=5 per group), and the virus challenge studies were done at least twice (n=10 per group). The response of each mouse was counted as an individual data point for statistical analysis. Data obtained from animal studies were examined by using two-way ANOVA from Prism; data were presented as mean±SEM and differences were considered significant at *$P<0.05$; $P<0.01$; *$P<0.001$.

Example 1 Preparation and Characterization of Monoglycosylated Chimeric HA

To design a universal vaccine, we first aimed to have a vaccine with broad protection against influenza A virus group 1 (H1 and H5 are the major subtypes while H2, H6, and H9 are minor). Therefore, the HA sequences from H1N1 viruses available from early 2009 to 2013 were used to create a consensus H1 sequence. The consensus H5 and consensus H1 were then used as the templates for vaccine design. In influenza virus replication, the HA precursor (HA0) is proteolytically cleaved into two subunits, HA1 and HA2; the HA1 subunit carries the 5-N-acetylneur-aminic acid (sialic acid) binding site, and the HA2 subunit is responsible for virus fusion with the host cellular membrane (FIG. 5A). On the other hand, HA can be divided into two structural domains, globular head and stem, based on the three-dimensional (3D) structure. The stem region contains the HA2 domain, the N-terminal 36~50 residues and a short stretch of the C terminus of the HA1 domain. We thus designed the vaccines based on various combinations of domains from H1 and H5. We first generated the swap H1/5 (H1 globular head and [H1+H5(HA2) stem], swap H5/1 (H5 globular head and [H5+H1(HA2) stem], and chimeric H5/1 (H5 globular head and H1 stem) for comparison (FIG. 1A and FIG. 5A). The result indicated that immunization with consensus H1N1 and swap H1/5 did not induce cross-protective activities, but the swap H5/1 and chimeric H5/1 did elicit cross-neutralization activity against H1N1 and H5N1 viruses (FIG. 1B). We next investigated whether this cross-protection was contributed from the CD8$^+$ T cell response, and found that granzyme B was more secreted in chimeric H5/1-immunized mice, suggesting that the chimeric H5/1 vaccine induced stronger CD8$^+$ T cell response compared to the swap H5/1 vaccine (FIG. 1C).

Example 2 Effect of Glycosylation on the Immune Response of Chimeric H5/1 (cHA)

To explore the immunogenicity of the chimeric H5/1 (cHA) vaccine with different glycosylation states, monoglycosylated cHA (cHA$_{mg}$) and fully glycosylated cHA (cHA$_{fg}$) vaccine were compared (FIG. 5). It is known that Endo-H is specific for high mannose but not complex-type glycans. The HA glycoprotein expressed in HEK293S cells, which are deficient in N-acetylglucosaminyltransferase I and produce glycoproteins with high-mannose-type N-glycans, was treated with Endo-H to cleave the N-glycans to a single GlcNAc residue. To generate cHA$_{mg}$, CHA was produced from human cells (HEK293S) and the purified cHA with high-mannose glycans was treated with Endo-H to remove the outer parts of N-glycans to produce the HA with only one N-acetylglucosamine (GlcNAc) linked to the asparagine residue of each glycosite. After Endo-H treatment, the mixture was passed through gel filtration to separate Endo-H from trimeric cHAme. After concentration, the cHAme proteins were subjected to sodium dodecyl sulfate-polyacrylamide gel electrophoresis (SDS/PAGE) and liquid chromatography-tandem mass spectrometry (LC-MS/MS) analyses to ensure purity and glycan composition (FIG. 5C). Since influenza HA exists as a trimer on the virus surface, gel filtration was performed to confirm that the cHA$_{fg}$ and cHA$_{mg}$ existed as a trimer (>200 kDa) (FIG. 5D). We also generated another fully glycosylated cHA$_{fg}$ from human cells (HEK293T) for comparison (FIG. 5B), and the cell culture yielded cHA$_{fg}$ with ~6 mg/L.

The N-linked glycosylation sites and the glycan profile of recombinant cHA$_{fg}$ and cHA$_{mg}$ were analyzed by LC-MS/MS showing seven glycosylation sites (N28, N40, N171, N182, N292, N303, and N497); the N-glycans of cHA$_{fg}$ were mostly complex type and cHA$_{mg}$ could be obtained in ~99% as a single glycoform with only GlcNAc at each of its N-glycosylation sites (FIG. 5E and Table 1).

TABLE 1

The N-linked glycan structures of cILA in fully-glycosylated and mono-glycosylated proteins analyzed by LC-MS/MS.

| Glycan name | Glycan Structure | N28 | | | N40 | | | N171 | | | N182 | | | N292 | | | N303 | | | N497 | | |
|---|---|---|---|---|---|---|---|---|---|---|---|---|---|---|---|---|---|---|---|---|---|---|
| | | cHA_fg | cHA_mg | | cHA_fg | cHA_mg | cHA_mg | cHA_fg | cHA_mg | cHA_mg | cHA_fg | cHA_mg | cHA_mg | cHA_fg | cHA_mg | cHA_mg | cHA_fg | cHA_mg | cHA_mg | cHA_fg | cHA_mg | cHA_mg |
| None | | 0% | 0% | | 0% | 0% | 0% | 0% | 0% | 0% | 0% | 0% | 0% | 0% | 0% | 0% | 0% | 1% | 0% | 0% | 0% | 0% |
| Deamidated | | 0% | 0% | | 3% | 0% | 0% | 0% | 0% | 0% | 0% | 0% | 0% | 0% | 0% | 0% | 1% | 0% | 0% | 7% | 0% | 0% |
| N | | 0% | 100% | | 0% | 0% | 100% | 0% | 0% | 95% | 0% | 0% | 100% | 0% | 0% | 100% | 1% | 0% | 99% | 0% | 0% | 100% |
| NF | | 0% | 0% | | 0% | 0% | 0% | 0% | 0% | 0% | 0% | 0% | 0% | 2% | 0% | 0% | 0% | 0% | 0% | 3% | 0% | 0% |
| Man5 | | 3% | 0% | | 3% | 0% | 0% | 0% | 0% | 0% | 0% | 0% | 0% | 0% | 0% | 0% | 6% | 0% | 0% | 0% | 0% | 0% |
| Man5NHS | | 0% | 0% | | 0% | 0% | 0% | 0% | 0% | 0% | 0% | 0% | 0% | 0% | 0% | 0% | 6% | 0% | 0% | 0% | 0% | 0% |
| N-N3H5S0F0 | | 0% | 0% | | 0% | 0% | 0% | 0% | 0% | 0% | 0% | 0% | 0% | 0% | 0% | 0% | 10% | 0% | 0% | 0% | 0% | 0% |

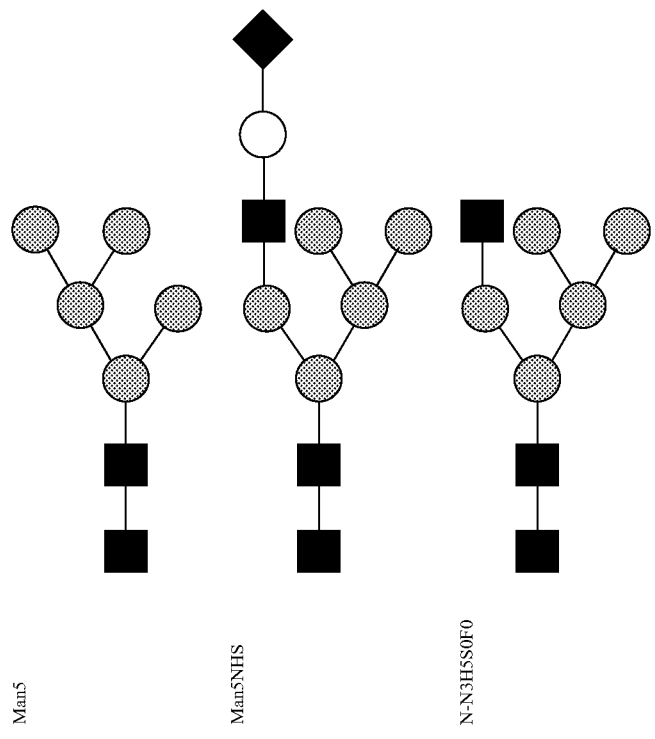

TABLE 1-continued

The N-linked glycan structures of cILA in fully-glycosylated and mono-glycosylated proteins analyzed by LC-MS/MS.

| Glycan name | Glycan Structure | N28 cHA$_{fg}$ | N28 cHA$_{mg}$ | N40 cHA$_{fg}$ | N40 cHA$_{mg}$ | N171 cHA$_{fg}$ | N171 cHA$_{mg}$ | N182 cHA$_{fg}$ | N182 cHA$_{mg}$ | N292 cHA$_{fg}$ | N292 cHA$_{mg}$ | N303 cHA$_{fg}$ | N303 cHA$_{mg}$ | N497 cHA$_{fg}$ | N497 cHA$_{mg}$ |
|---|---|---|---|---|---|---|---|---|---|---|---|---|---|---|---|
| N-N3H5S1F0 | | 0% | 0% | 0% | 0% | 0% | 0% | 0% | 0% | 0% | 0% | 10% | 0% | 0% | 0% |
| N-N3H5S0F1 | | 1% | 0% | 0% | 0% | 0% | 0% | 0% | 0% | 0% | 0% | 0% | 0% | 0% | 0% |
| N-N3H5S1FE1 | | 0% | 0% | 0% | 0% | 0% | 0% | 0% | 0% | 0% | 0% | 3% | 0% | 0% | 0% |
| N-N3H4S0F0 | | 0% | 0% | 0% | 0% | 0% | 0% | 0% | 0% | 0% | 0% | 2% | 0% | 0% | 0% |
| NNH3NN | | 0% | 0% | 0% | 0% | 0% | 0% | 2% | 0% | 0% | 0% | 0% | 0% | 0% | 0% |

TABLE 1-continued

The N-linked glycan structures of cILA in fully-glycosylated and mono-glycosylated proteins analyzed by LC-MS/MS.

| Glycan name | Glycan Structure | N28 cHA$_{fg}$ | N28 cHA$_{mg}$ | N40 cHA$_{fg}$ | N40 cHA$_{mg}$ | N171 cHA$_{fg}$ | N171 cHA$_{mg}$ | N182 cHA$_{fg}$ | N182 cHA$_{mg}$ | N292 cHA$_{fg}$ | N292 cHA$_{mg}$ | N303 cHA$_{fg}$ | N303 cHA$_{mg}$ | N497 cHA$_{fg}$ | N497 cHA$_{mg}$ |
|---|---|---|---|---|---|---|---|---|---|---|---|---|---|---|---|
| N4NN | | 0% | 0% | 0% | 0% | 0% | 0% | 0% | 0% | 0% | 0% | 0% | 0% | 0% | 0% |
| NNH3NNF1-G0 | | 0% | 0% | 0% | 0% | 0% | 0% | 1% | 0% | 0% | 0% | 0% | 0% | 0% | 0% |
| Man6N1 | | 1% | 0% | 5% | 0% | 0% | 0% | 0% | 0% | 0% | 0% | 9% | 0% | 0% | 0% |
| BiF1-I | | 0% | 0% | 0% | 0% | 0% | 0% | 0% | 0% | 2% | 0% | 1% | 0% | 2% | 0% |

TABLE 1-continued

The N-linked glycan structures of cILA in fully-glycosylated and mono-glycosylated proteins analyzed by LC-MS/MS.

| Glycan name | Glycan Structure | N28 | | N40 | | N171 | | N182 | | N292 | | N303 | | N497 | |
|---|---|---|---|---|---|---|---|---|---|---|---|---|---|---|---|
| | | $cHA_{fg}$ | $cHA_{mg}$ | $cHA_{fg}$ | $cHA_{mg}$ | $cHA_{fg}$ | $cHA_{mg}$ | $cHA_{fg}$ | $cHA_{mg}$ | $cHA_{fg}$ | $cHA_{mg}$ | $cHA_{fg}$ | $cHA_{mg}$ | $cHA_{fg}$ | $cHA_{mg}$ |
| BiS1 | | 0% | 0% | 0% | 0% | 0% | 0% | 0% | 0% | 0% | 0% | 0% | 0% | 0% | 0% |
| BiS1-H | | 0% | 0% | 0% | 0% | 0% | 0% | 10% | 0% | 0% | 0% | 13% | 0% | 0% | 0% |
| BiS1F1-H | | 0% | 0% | 0% | 0% | 0% | 0% | 0% | 0% | 1% | 0% | 0% | 0% | 0% | 0% |
| BiS2 | | 0% | 0% | 0% | 0% | 0% | 0% | 0% | 0% | 0% | 0% | 1% | 0% | 0% | 0% |
| BiS2-H | | 0% | 0% | 0% | 0% | 0% | 0% | 3% | 0% | 0% | 0% | 0% | 0% | 0% | 0% |

TABLE 1-continued

The N-linked glycan structures of cILA in fully-glycosylated and mono-glycosylated proteins analyzed by LC-MS/MS.

| Glycan name | Glycan Structure | N28 cHA$_{fg}$ | N28 cHA$_{mg}$ | N40 cHA$_{fg}$ | N40 cHA$_{mg}$ | N171 cHA$_{fg}$ | N171 cHA$_{mg}$ | N182 cHA$_{fg}$ | N182 cHA$_{mg}$ | N292 cHA$_{fg}$ | N292 cHA$_{mg}$ | N303 cHA$_{fg}$ | N303 cHA$_{mg}$ | N497 cHA$_{fg}$ | N497 cHA$_{mg}$ |
|---|---|---|---|---|---|---|---|---|---|---|---|---|---|---|---|
| BiS2N1 | | 0% | 0% | 0% | 0% | 0% | 0% | 0% | 0% | 0% | 0% | 0% | 0% | 0% | 0% |
| Bi | | 0% | 0% | 0% | 0% | 0% | 0% | 2% | 0% | 0% | 13% | 0% | 0% | 0% | 0% |
| N-N5H4S0F0 | | 0% | 0% | 0% | 0% | 0% | 0% | 21% | 0% | 0% | 0% | 0% | 0% | 0% | 0% |
| N-N5H3S0F0 | | 0% | 0% | 0% | 0% | 0% | 0% | 38% | 0% | 0% | 0% | 0% | 0% | 0% | 0% |
| N-N5H3S0F1 | | 0% | 0% | 0% | 0% | 0% | 0% | 10% | 0% | 0% | 0% | 0% | 0% | 0% | 0% |

TABLE 1-continued

The N-linked glycan structures of cILA in fully-glycosylated and mono-glycosylated proteins analyzed by LC-MS/MS.

| Glycan name | Glycan Structure | N28 cHA$_{fg}$ | N28 cHA$_{mg}$ | N40 cHA$_{fg}$ | N40 cHA$_{mg}$ | N171 cHA$_{fg}$ | N171 cHA$_{mg}$ | N182 cHA$_{fg}$ | N182 cHA$_{mg}$ | N292 cHA$_{fg}$ | N292 cHA$_{mg}$ | N303 cHA$_{fg}$ | N303 cHA$_{mg}$ | N497 cHA$_{fg}$ | N497 cHA$_{mg}$ |
|---|---|---|---|---|---|---|---|---|---|---|---|---|---|---|---|
| BiF1 | | 6% | 0% | 12% | 0% | 0% | 0% | 0% | 0% | 7% | 0% | 8% | 0% | 11% | 0% |
| Bi-H | | 0% | 0% | 0% | 0% | 0% | 0% | 5% | 0% | 0% | 0% | 0% | 0% | 0% | 0% |
| BiN1 | | 0% | 0% | 0% | 0% | 0% | 0% | 0% | 0% | 0% | 0% | 1% | 0% | 0% | 0% |
| BiN1F1-H | | 0% | 0% | 2% | 0% | 8% | 0% | 0% | 0% | 1% | 0% | 3% | 0% | 7% | 0% |
| BiN1F2-H | | 0% | 0% | 0% | 0% | 2% | 0% | 0% | 0% | 0% | 0% | 0% | 0% | 0% | 0% |

TABLE 1-continued

The N-linked glycan structures of cILA in fully-glycosylated and mono-glycosylated proteins analyzed by LC-MS/MS.

| Glycan name | Glycan Structure | N28 | | N40 | | N171 | | N182 | | N292 | | N303 | | N497 | |
|---|---|---|---|---|---|---|---|---|---|---|---|---|---|---|---|
| | | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ |
| BiN1F1 | | 1% | 0% | 14% | 0% | 9% | 0% | 0% | 0% | 9% | 0% | 0% | 0% | 31% | 0% |
| BiS1F1 | | 3% | 0% | 25% | 0% | 6% | 0% | 0% | 0% | 34% | 0% | 0% | 0% | 38% | 0% |
| BiS2F1 | | 0% | 0% | 0% | 0% | 7% | 0% | 0% | 0% | 21% | 0% | 9% | 0% | 0% | 0% |
| N-N5H4S1F1 | | 0% | 0% | 0% | 0% | 23% | 0% | 0% | 0% | 0% | 0% | 0% | 0% | 0% | 0% |

TABLE 1-continued
The N-linked glycan structures of cILA in fully-glycosylated and mono-glycosylated proteins analyzed by LC-MS/MS.
| Glycan name | Glycan Structure | N28 | | N40 | | N171 | | N182 | | N292 | | N303 | | N497 | |
|---|---|---|---|---|---|---|---|---|---|---|---|---|---|---|---|
| | | $cHA_{fg}$ | $cHA_{mg}$ | $cHA_{fg}$ | $cHA_{mg}$ | $cHA_{fg}$ | $cHA_{mg}$ | $cHA_{fg}$ | $cHA_{mg}$ | $cHA_{fg}$ | $cHA_{mg}$ | $cHA_{fg}$ | $cHA_{mg}$ | $cHA_{fg}$ | $cHA_{mg}$ |
| BiN1S1F1 | | 0% | 0% | 0% | 0% | 0% | 0% | 0% | 0% | 10% | 0% | 0% | 0% | 0% | 0% |
| BiN1S1-H | | 0% | 0% | 0% | 0% | 0% | 0% | 2% | 0% | 0% | 0% | 0% | 0% | 0% | 0% |
| N-N5H4S1F2 | | 0% | 0% | 0% | 0% | 16% | 0% | 0% | 0% | 0% | 0% | 0% | 0% | 0% | 0% |
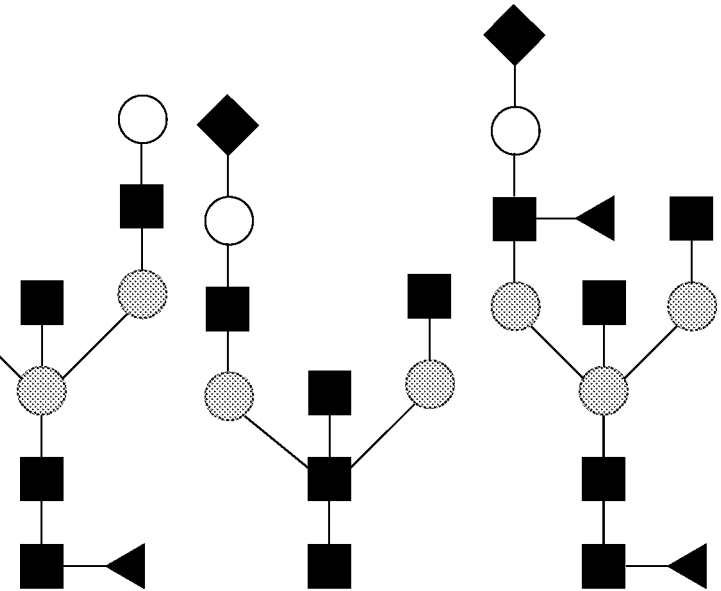

TABLE 1-continued

The N-linked glycan structures of cILA in fully-glycosylated and mono-glycosylated proteins analyzed by LC-MS/MS.

| Glycan name | Glycan Structure | N28 | | N40 | | N171 | | N182 | | N292 | | N303 | | N497 | |
|---|---|---|---|---|---|---|---|---|---|---|---|---|---|---|---|
| | | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ |
| BiN1SNF1 | | 0% | 0% | 1% | 0% | 6% | 0% | 0% | 0% | 0% | 0% | 0% | 0% | 0% | 0% |
| N-N5H4S2F1 | | 0% | 0% | 0% | 0% | 15% | 0% | 0% | 0% | 0% | 0% | 0% | 0% | 0% | 0% |
| TriF1 | | 43% | 0% | 2% | 0% | 0% | 0% | 0% | 0% | 0% | 0% | 0% | 0% | 0% | 0% |

TABLE 1-continued

The N-linked glycan structures of cILA in fully-glycosylated and mono-glycosylated proteins analyzed by LC-MS/MS.

| Glycan name | Glycan Structure | N28 | | N40 | | N171 | | N182 | | N292 | | N303 | | N497 | |
|---|---|---|---|---|---|---|---|---|---|---|---|---|---|---|---|
| | | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ |
| TriS1F1 | | 38% | 0% | 11% | 0% | 0% | 0% | 0% | 0% | 3% | 0% | 0% | 0% | 1% | 0% |
| TriN1F1 | | 3% | 0% | 0% | 0% | 0% | 0% | 0% | 0% | 0% | 0% | 0% | 0% | 0% | 0% |
| BiF1N1S2 | | 0% | 0% | 0% | 0% | 0% | 0% | 0% | 0% | 1% | 0% | 0% | 0% | 0% | 0% |

TABLE 1-continued

The N-linked glycan structures of cILA in fully-glycosylated and mono-glycosylated proteins analyzed by LC-MS/MS.

| Glycan name | Glycan Structure | N28 | | N40 | | N171 | | N182 | | N292 | | N303 | | N497 | |
|---|---|---|---|---|---|---|---|---|---|---|---|---|---|---|---|
| | | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ |
| TriS2F1 | | 0% | 0% | 0% | 0% | 0% | 0% | 0% | 0% | 0% | 0% | 0% | 0% | 0% | 0% |
| TetraF1 | | 0% | 0% | 2% | 0% | 0% | 0% | 0% | 0% | 4% | 0% | 0% | 0% | 0% | 0% |
| TetraS1F1 | | 1% | 0% | 7% | 0% | 0% | 0% | 0% | 0% | 0% | 0% | 0% | 0% | 0% | 0% |

TABLE 1-continued

The N-linked glycan structures of cILA in fully-glycosylated and mono-glycosylated proteins analyzed by LC-MS/MS.

| Glycan name | Glycan Structure | N28 | | N40 | | N171 | | N182 | | N292 | | N303 | | N497 | |
|---|---|---|---|---|---|---|---|---|---|---|---|---|---|---|---|
| | | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ | cHA$_{fg}$ | cHA$_{mg}$ |
| TetraS2F1 | | 0% | 0% | 11% | 0% | 0% | 0% | 0% | 0% | 0% | 0% | 0% | 0% | 0% | 0% |
| TetraH1S2 | | 0% | 0% | 2% | 0% | 2% | 0% | 0% | 0% | 0% | 0% | 0% | 0% | 0% | 0% |
| Others | | 0% | 0% | 0% | 0% | 5% | 0% | 6% | 0% | 5% | 0% | 3% | 0% | 0% | 0% |

Example 3 Cross-Reactivity of Antisera from Mice Immunized with Fully Glycosylated Chimeric H5/1 (cHA$_{fg}$) and Monoglycosylated Chimeric H5/1 (cHA$_{mg}$)

Figure 1:
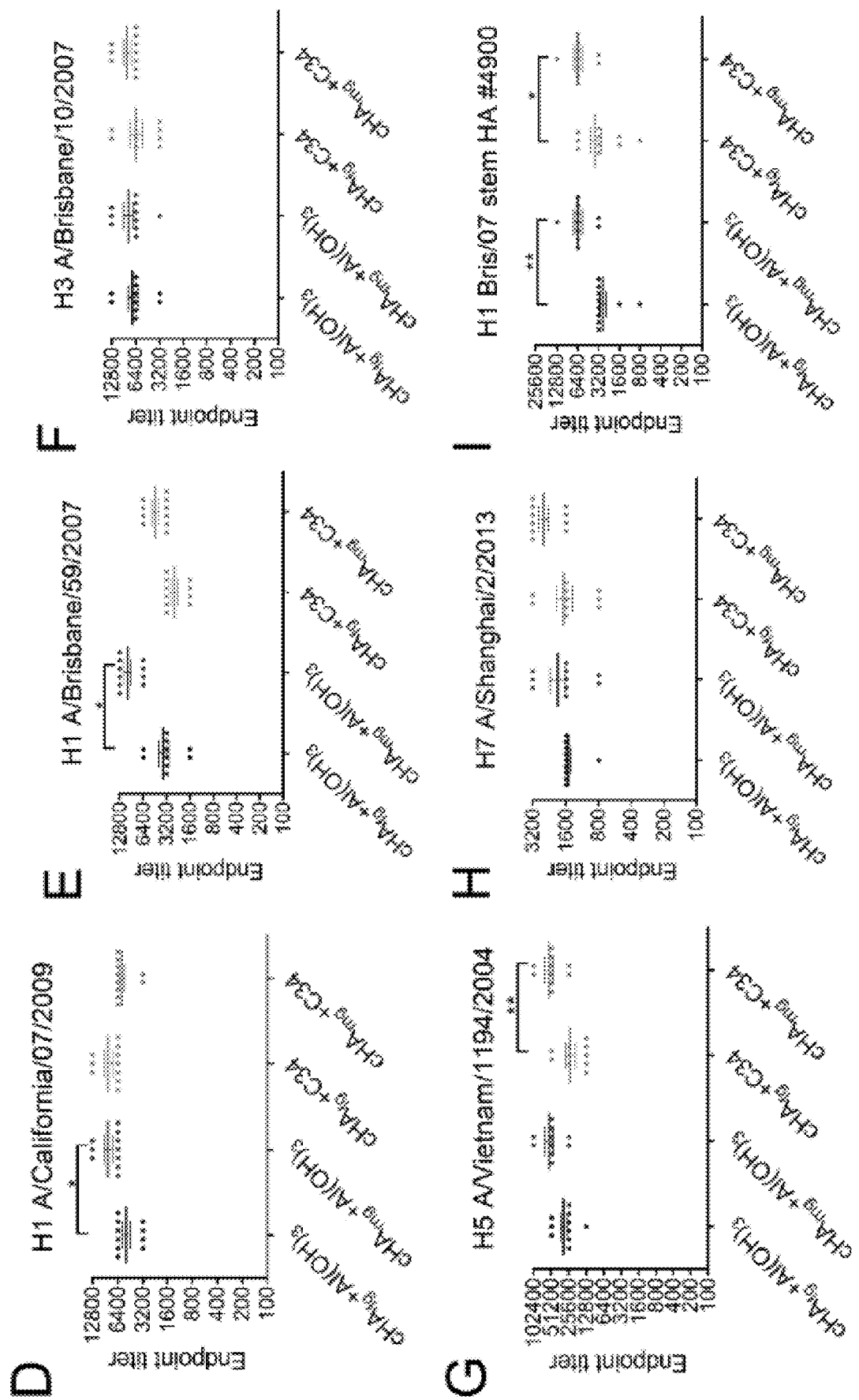
FIGS. 1 (A) to (I). The chimeric H5/1 construct with consensus H5 globular head and consensus H1 stem (cHA)

To evaluate the binding activity of antibody elicited by cHA constructs, BALB/c mice were immunized intramuscularly with 20 µg of cHA$_{fg}$ or cHA$_{mg}$ protein adjuvanted with Al(OH)$_3$ or C34, an analog of α-galactosylceramide (α-GalCer). The mice were immunized at weeks 0, 2, and 4, and HA-induced serum was obtained on days 28 and 42 and measured using enzyme-linked immunosorbent assay (ELISA) with various recombinant HAs (FIG. 6). Comparing to the maximum dilution of antisera after two immunizations, three immunizations indeed produced antiserum with higher titers of HA-specific antibodies (FIG. 1 D-I and FIG. 7), and vaccination with cHA$_{mg}$ induced better antibody response compared to cHA$_{fg}$ (FIGS. 1 D, E, and G). In addition, the antiserum from cHA$_{mg}$ showed slightly better binding to H3 and H7 HA proteins (FIGS. 1 F and H), and no significant differences were observed between Al(OH)$_3$ and C34 adjuvants. These data indicate that the cHA vaccine could elicit cross-reactive antibodies recognizing the HA from H1N1, H3N2, H5N1, as well as H7N9 strains.

F10 is a broadly neutralizing IgG antibody known to target the stem region of HA, which is highly conserved among various subtypes of influenza viruses. To compare the binding of F10 to recombinant H1, H5, and cHA, the binding avidities of F10 to various HAs were measured, and the results showed that F10 could bind H1, H5, and cHA proteins (FIG. 8). To investigate if F10-like antibodies were elicited by cHA vaccination, the binding of cHA-induced serum to HA stem no. 4900 was measured by using ELISA. The results showed that the cHA$_{mg}$ vaccine can induce higher stem-specific antibody titer than cHA$_{fg}$ (FIG. 11 and FIG. 7F), and better results were observed with C34-adjuvanted cHA vaccine (FIG. 1I), which in-duced more stem-specific antibodies.

Example 4 Vaccination of Mice with cHA$_{mg}$ and Adjuvant C34 Elicits Strong CD4$^+$ and CD8$^+$ T-Cell Responses and Antibody-Dependent Effector Functions, and Neutralizing Activities Against H1, H3, H5 Viruses as Well as their Subtypes Besides antibody-mediated neutralization, Fc-mediated effector functions also play an important role in protection against influenza infection. We therefore examined whether the antibodies would induce Fc receptor-mediated immune response. The mouse-adapted ADCC assay was performed using Jurkat effector cells expressing FcγRIII to evaluate the ADCC activities of the sera from cHA$_{fg}$- and cHA$_{mg}$-immunized mice (FIG. 2). As expected, the serum from cHA$_{fg}$- or cHA$_{mg}$-vaccinated mice induced comparable levels of ADCC activities against H5N1 NIBRG14 (A/Vietnam/1194/2004), NIBRG23 (A/Turkey/1/2005), RG5 (A/Anhui/1/2005), or RG2 (A/Indonesia/5/2005) viruses. Interestingly, better ADCC activities were observed in the cHA$_{mg}$ group adjuvanted with Al(OH)$_3$ (FIG. 2B), and similar results were observed in experiments against H1N1 A/California/07/2009, A/Brisbane/59/2007, A/Solomon Islands/3/2006, A/New Caledonia/20/1999 (FIG. 2A), H3N2 A/Wisconsin/67/2005, and A/Victoria/361/2011 viruses (FIG. 2C).

To evaluate the role of antigen-specific cytokine-secreting cells in cHA-immunized mice, the splenocytes were collected after two and three immunizations and the IFN-γ, IL-4, and granzyme B (GzB)-secreting cells were estimated by enzyme-linked immune absorbent spot (ELISpot) assays with specific peptides from HA for stimulation. As shown in FIG. 3, the cHA$_{fg}$ and cHA$_{mg}$ vaccines adjuvanted with Al(OH)$_3$ produced similar levels of cytokine-secreting cells. However, more CD4$^+$/IFN-γ$^+$ Th1 cells (FIG. 3A), CD4$^+$/IL-4$^+$ Th2 (FIG. 3B), and CD8$^+$ GzB-secreting cells (FIG. 3C) were elicited in cHA$_{mg}$ vaccination adjuvanted with C34 than with Al(OH)$_3$. These results confirmed that cHA$_{mg}$ adjuvanted with C34 could stimulate more CD4$^+$ T helper response and stronger CD8$^+$ cytotoxicity effects compared to cHA$_{fg}$.

To evaluate the dose dependence of C34 on antibody titers and cell-mediated immunity, mice were immunized intramuscularly with cHA$_{fg}$ adjuvanted with three different doses of C34 at 0.5, 2, and 10 µg. The result indicated that cHA$_{fg}$ adjuvanted with 2 µg of C34 induced higher titers than with 0.5 and 10 µg of C34 after two or three immunizations (FIG. 9). In addition, the cHA$_{fg}$ vaccine adjuvanted with 2 µg of C34 induced more IFN-γ than with 0.5 and 10 µg of C34 (FIG. 10A) and 2 and 10 µg of C34 induced more IL-4 than with 0.5 µg of C34 after three immunizations (FIG. 10B). On the other hand, there were no differences with regard to the increase in CD8$^+$ GzB-secreting cells when the cHA$_{fg}$ vaccine was adjuvanted with 0.5, 2, or 10 µg of C34 after two and three immunizations (FIG. 10C). Based on these observations, 2 µg of C34 were used throughout the experiments.

The neutralizing activities of cHA-induced antisera were further investigated. The antisera from cHA$_{mg}$ vaccination were shown to have better neutralization activities against the homologous viruses H1N1 A/California/07/2009 (FIG. 3D) and heterologous H5N1 NIBRG14 (A/Vietnam/1194/2004), NIBRG23 (A/Turkey/1/2005), RG5 (A/Anhui/1/2005), or RG2 (A/Indonesia/5/2005) (FIG. 3E). In addition, the antisera from mice vaccinated with cHA$_{mg}$ exhibit significant neutralizing activities against heterologous viruses H1N1 A/Brisbane/59/2007, A/New Caledonia/20/1999, and A/Solomon Islands/3/2006 (FIG. 3D). The antisera from cHA-immunized mice were clearly able to block the infection of H1N1 and H5N1 viruses, and the neutralizing activity of cHA$_{mg}$ was in general better than cHA$_{fg}$, particularly against the heterologous viruses.

Example 5 Vaccination of Mice with cHA$_{mg}$/C34 Provides Cross-Protection Against H1N1 and H5N1 as Well as their Subtypes in the Challenge Study In order to assess whether cHA$_{mg}$ vaccination provides broadly cross-protective immunity against various H1N1 and H5N1 viruses, the vaccinated mice were challenged by intranasal inoculation with lethal doses of multiple H1N1 and H5N1 viruses, and the efficacy of vaccine protection was evaluated for 14 d by recording the survival rate and body weight change (FIG. 4 and FIG. 11). For the mice challenged with H1N1 A/California/07/2009 viruses, all cHA vaccines offered 100% protection (FIG. 4A). In addition, the mice immunized with C34-adjuvanted cHA$_{mg}$ showed minimal amounts of weight loss compared with cHA$_{fg}$ (FIG. 11A). The mice immunized with C34-adjuvanted cHA$_{fg}$ only gave 30% protection against A/New Caledonia/1999 challenges; however, the cHA$_{mg}$ vaccine adjuvanted with C34 offered 90% protection against crossstrain A/New Caledonia/1999 viruses, and similar results were observed in Al(OH)$_3$-adjuvanted cHA vaccination (FIG. 4B). For the mice challenged with cross-strain A/WSN/1933 viruses, all mice immunized with Al(OH)$_3$- adjuvanted cHA survived; however, the mice immunized with C34-adjuvanted cHA$_{fg}$ only gave 80% protection (FIG. 4C). The lethal challenges were also performed with A/Solomon Islands/03/2006. All mice immunized with Al(OH)$_3$-adjuvanted cHA showed lower protection; however, the mice immunized with C34-adjuvanted cHA$_{mg}$ showed better protection against cross-strain A/Solomon Islands/03/2006 viruses (FIG. 4D). For the mice challenged with H5N1 NIBRG14 (A/Vietnam/1194/2004) and NIBRG23 (A/Turkey/1/2005), all immunized mice survived (FIGS. 4 E and F). The body weight changes after viral challenges were also evaluated (FIG. 11). The data showed that cHA was effective in eliciting a significant protective immunity against various H1N1 and H5N1 viruses, and cHA$_{mg}$ provides a broader cross-protection ability compared to cHA$_{fg}$.

Development of universal influenza vaccine to provide protection against multiple strains and subtypes of influenza viruses is of current interest, and the epitopes used for universal vaccine development include the highly conserved ectodomain of M2 containing 24 nonglycosylated amino acids, the nucleoprotein NP, and the various HA constructs which have been shown to induce higher titers of broadly neutralizing antibodies to target the HA-stem region or block viral entry. For example, a soluble trimeric HA (mini-HA) vaccine with realigned stem subunit was shown to completely protect mice from lethal challenge by heterologous and heterosubtypic viruses, and a chimeric HA vaccination with DNA prime-protein boost and exposure to the same stem region and divergent exotic head domains was shown to elicit broadly protective stem-specific antibodies. However, the result showed that CD8$^+$ T cells did not play a key role in the cross-protective activities. Although DNA vaccines are promising, they are still in the early stage of development. In this study, the cHA constructs that express the consensus H5 of globular head and the consensus H1 of stem region were designed to mimic the real status of influenza virus transmitting from avian virus to human. Both fully glycosylated cHA$_{fg}$ and monoglycosylated cHA$_{mg}$ were prepared for comparison, and the result showed that the cHA$_{mg}$ vaccine elicited higher titers of cross-reactive antibodies against H1, H3, H5, and H7 subtypes (FIG. 1 D-H) through CD4$^+$ and CD8$^+$ T cell responses (FIG. 3A-C).

The glycosylation of HA was shown to play an important role in protein folding and stability and in modulating its biological activities, including shielding the antigenic sites from neutralizing antibodies to reduce the immunogenicity. In addition, hyperglycosylated HA was evolved to mask the antigenic sites in the highly variable head domain and the immune response was thus redirected toward the conserved stem region. In our results, the neutralization activities of the cHA$_{mg}$ antiserum were significantly superior to the cHA$_{fg}$-induced antiserum, especially against the heterologous H1N1 A/Brisbane/59/2007, A/Solomon Islands/03/2006, and A/New Caledonia/20/1999 (FIG. 3D). The broader neutralizing activities of cHA$_{mg}$ vaccine is probably due its induction of more antibody variants as reported previously. IgG is the predominant antibody present in mouse and is the major subtype of HA-specific antibodies with high avidity to the FcγRIII receptor on immune cells to induce ADCC. We showed that immunization with cHA$_{mg}$ induced higher ADCC and more stem-specific antibodies with better protection activity (FIGS. 1/and 2), consistent with the studies showing that ADCC is necessary for influenza protection in vivo. Aluminum hydroxide (Alum) was known to stimulate Th2 response and was approved by the FDA for use as vaccine adjuvant; however, its mode of action has not been well studied. The glycolipid C34 is a ligand for and presented by CD1d on dendritic cells to interact with a receptor on invariant natural killer T (iNKT) cells, leading to the stimulation of iNKT cells to produce Th1 cytokines (e.g., IFN-γ) with adjuvant effect and Th2 cytokines (e.g., IL-4) with class-switch activity. In our results, the number of IFN-γ (Th1 cytokine), IL-4 (Th2 cytokine)-secreting cells, and the granzyme B-producing CD8$^+$ T cells were significantly increased by immunization with cHA$_{mg}$ adjuvanted with C34 than with Al(OH)$_3$ (FIG. 3A-C).

In summary, development of next-generation influenza vaccines with broad-protective immune responses is of current interest, and some promising results have been reported, making the development of a universal vaccine within reach. In an effort directed toward this goal, we have successfully demonstrated in this study a proof of principle that the monoglycosylated cHA vaccine with consensus H5 head and consensus H1 stem is an effective influenza vaccine exhibiting a broad protection activity against heterologous influenza viruses, including H1, H3, H5, and H7 viruses and subtypes in the neutralizing study and H1N1, H5N1, and subtypes in the challenge study. With the success in the development of a broadly protective vaccine against different strains and subtypes of influenza A virus, we aim to use the strategy developed in this study to design a broader universal vaccine against influenza A and B viruses.

What is claimed is:

1. An immunogenic composition comprising a fully glycosylated chimeric influenza virus hemagglutinin (HA) polypeptide and an adjuvant;
    wherein the fully glycosylated chimeric influenza virus HA polypeptide comprising an amino acid sequence of SEQ ID NO: 4;
    wherein the fully glycosylated chimeric influenza virus HA polypeptide has complex type N-glycans at N28, N40, N171, N182, N292, N303, and N497; and
    wherein the adjuvant is selected from the group consisting of Al(OH)$_3$, AlPO$_4$, an analog of α-galactosylceramide (α-GalCer), squalene and QS21.

2. The immunogenic composition of claim 1, wherein:

the N-glycans at N28 comprise (TriF1)

and (TriS1F1);

the N-glycans at N40 comprise (BiF1)

and (BiS1F1);

the N-glycans at N171 comprise (N-N5H4S1F1)

and (N-N5H4S1F2);

the N-glycans at N182 comprise (N-N5H4S0F0)

and (N-N5H3S0F0);

the N-glycans at N292 comprise (BiS1F1)

and (BiS2F1);

the N-glycans at N303 comprise
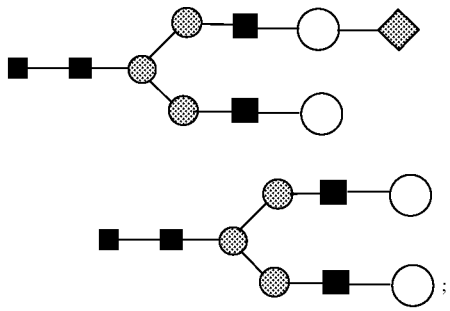
and
the N-glycans at N497 comprise
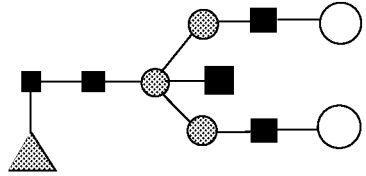
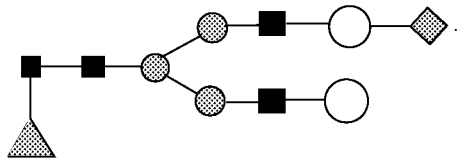
3. The immunogenic composition of claim 1, wherein the adjuvant is Al(OH)$_3$.
4. The immunogenic composition of claim 1, wherein the analog of α-galactosylceramide is C34.
5. The immunogenic composition of claim 1, wherein the fully glycosylated chimeric influenza virus HA polypeptide is exist